(12) United States Patent
Dorwald et al.

(10) Patent No.: US 6,417,218 B1
(45) Date of Patent: Jul. 9, 2002

(54) SUBSTITUTED IMIDAZOLES, THEIR PREPARATION AND USE

(75) Inventors: Florencio Zaragoza Dorwald, Ballerup; Knud Erik Andersen, Brøndby, both of (DK)

(73) Assignees: Novo Nordisk A/S, Bagsvaerd (DK); Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 09/484,621

(22) Filed: Jan. 18, 2000

Related U.S. Application Data
(60) Provisional application No. 60/116,510, filed on Jan. 20, 1999.

(30) Foreign Application Priority Data

Jan. 18, 1999 (DK) .......................................... 1999 00054

(51) Int. Cl.$^7$ ..................... A61K 31/415; C07D 233/56
(52) U.S. Cl. ..................... 514/399; 514/400; 548/345.5
(58) Field of Search ....................... 548/345.5; 514/399, 514/400

(56) References Cited

U.S. PATENT DOCUMENTS

| | | | | |
|---|---|---|---|---|
| 3,868,458 A | | 2/1975 | Baker et al. ................. | 424/273 |
| 4,535,165 A | * | 8/1985 | Moore ......................... | 548/204 |
| 4,588,738 A | * | 5/1986 | Cozzi et al. ................. | 514/399 |
| 4,634,705 A | * | 1/1987 | Debernardis et al. ....... | 514/256 |
| 4,689,339 A | * | 8/1987 | Karjalainen, I et al. .... | 514/396 |
| 4,767,778 A | | 8/1988 | Arrang et al. ............... | 514/397 |
| 4,812,473 A | * | 3/1989 | Kuwano et al. ............. | 514/396 |
| 5,026,868 A | * | 6/1991 | Karjalainen, II et al. ... | 548/346 |
| 5,091,539 A | * | 2/1992 | Makisumi et al. ....... | 548/267.8 |
| 5,292,887 A | * | 3/1994 | Karjalainbn et al. ........ | 514/396 |
| 5,578,616 A | | 11/1996 | Aslanian et al. | |

FOREIGN PATENT DOCUMENTS

| | | |
|---|---|---|
| DE | 2 260 025 | 6/1973 |
| DE | 2944661 | * 5/1981 |
| EP | 0 214 058 | 3/1987 |
| EP | 0 338 939 | 10/1989 |
| EP | 0 458 661 | 11/1991 |
| EP | 0 494 010 | 7/1992 |
| EP | 0 531 219 | 3/1993 |
| GB | 2 158 440 | 11/1985 |
| JP | 41-20346 | * 11/1966 |
| JP | 2-83372 | * 3/1996 |
| WO | WO 91/17146 | 11/1991 |
| WO | WO 92/15567 | 9/1992 |
| WO | WO 93/12093 | 6/1993 |
| WO | WO 93/12107 | 6/1993 |
| WO | WO 93/12108 | 6/1993 |
| WO | WO 93/14070 | 7/1993 |
| WO | WO 93/20061 | 10/1993 |
| WO | WO 94/17058 | 8/1994 |
| WO | WO 95/06037 | 3/1995 |
| WO | WO 95/11894 | 5/1995 |
| WO | WO 95/14007 | 5/1995 |
| WO | WO 96/38141 | 12/1996 |
| WO | WO 96/38142 | 12/1996 |
| WO | WO 96/40126 | 12/1996 |
| WO | WO 98/07718 | 2/1998 |

OTHER PUBLICATIONS

Chemical Abstract, vol. 110, No. 192830, p. 751 (1989).
Chemical Abstract, vol. 116, No. 128771, pp. 876–877 (1992).
Chemical Abstract, vol. 84, No. 73190 p. 362 (1976).
Chemical Abstract, vol. 80, No. 82810, p. 389 (1974).
Tanaka et al., I, Japanese Abstract of JP 02238465, No. 1991:418563 CAPLUS.
Tanaka et al.II, Japanese Abstract of JP 03103867, No. 1991:643977 CAPLUS.
Barocelli et al., Pharmaceutical Sci., vol. 2, pp. 369–373 (1996).
Shih et al., J. Med. Chem., vol. 38, pp. 1593–1599 (1995).
Katritzky et al., J. Chem. Soc. Perkin Trans., vol. 1, pp. 1139–1145 (1989).
Stark et al., Drugs of the Future, vol. 21, No. 5, pp. 507–520 (1996).
Singh et al., Progress in Drug Research, vol. 45, pp. 107–165 (1995).

* cited by examiner

*Primary Examiner*—Floyd D. Higel
*Assistant Examiner*—Ebenezer Sackey
(74) *Attorney, Agent, or Firm*—Reza Green, Esq.; Peter J. Waibel, Esq.

(57) ABSTRACT

A class of substituted imidazole compounds of formula I

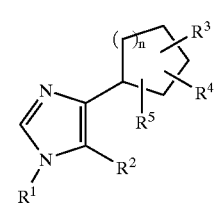

(I)

methods for their preparation, pharmaceutical compositions comprising them and use thereof in the treatment of disorders related to the histamine H3 receptor are disclosed. More particularly, these compounds possess histamine H3 receptor antagonistic activity and are thus useful for the treatment of disorders in which a histamine H3 receptor blockade is beneficial.

30 Claims, No Drawings

US 6,417,218 B1

SUBSTITUTED IMIDAZOLES, THEIR PREPARATION AND USE

CROSS-REFERENCE TO RELATED APPLICATIONS

This application claims priority under 35 U.S.C. 119 of U.S. provisional application no. 60/116,510 filed Jan. 20, 1999 and Danish application no. PA 1999 00054 filed Jan. 18, 1999, the contents of which are fully incorporated herein by reference.

BACKGROUND OF THE INVENTION

1. Field of the Invention

The present invention relates to novel substituted imidazoles, to methods for their preparation, to the use of these compounds as medicaments, to pharmaceutical compositions comprising the compounds, and to a method of treatment employing these compounds and compositions. The present compounds show a high and selective binding affinity to the histamine H3 receptor indicating a histamine H3 receptor antagonistic or agonistic activity. As a result, the compounds are useful for the treatment of disorders related to the histamine H3 receptor. More particularly, the present compounds possess a histamine H3 receptor antagonistic activity and accordingly are useful for the treatment of disorders in which a histamine H3 receptor blockade is beneficial.

2. Description of the Related Art

The histamine H3 receptor is known and of current interest for the development of new medicaments (see e.g. Stark, H.; Schlicker, E.; Schunack, W., *Drugs Fut.* 1996, 21, 507–520; Leurs, R.; Timmerman, H.; Vollinga, R. C., *Progress in Drug Research* 1995, 45, 107–165). The histamine H3 receptor is a presynaptic autoreceptor located in both the central and the peripheral nervous system, the skin and in organs such as the lung, the intestine, probably the spleen and the gastrointestinal tract. The histamine H3 receptor has been demonstrated to regulate the release of histamine and also of other neurotransmitters such as serotonin and acetylcholine. A histamine H3 receptor antagonist would therefore be expected to increase the release of these neurotransmitters in the brain. A histamine H3 receptor agonist, on the contrary, leads to an inhibition of the biosynthesis and release of histamine and also of other neurotransmitters such as serotonin and acetylcholine. These findings suggest that histamine H3 receptor agonists and antagonists could be important mediators of neuronal activity. Accordingly, the histamine H3 receptor is an important target for new therapeutics.

Several publications disclose the preparation and use of histamine H3 agonists and antagonists.

Thus, U.S. Pat. No. 4,767,778 (corresponding to EP 214 058), EP 338 939, EP 531 219, EP 458 661, WO 91/17146, WO 92/15567, WO 96/38142 and WO 96/38141 disclose imidazole derivatives having histamine H3 receptor agonistic or antagonistic activity. However, none of these derivatives has a five or six membered carbocyclic ring optionally containing one or two double bonds directly attached to the 4-position of the imidazole ring such as is the case in the present compounds.

WO 93/12093 disclose imidazole derivatives having histamine H3 receptor agonistic or antagonistic activity. These derivatives have a six or seven membered nitrogen containing ring in the 4-position of the imidazole ring which nitrogen containing ring is attached to the imidazole ring via a methylene group. EP 197 840, EP 494 010, WO 95/11894, WO 93/20061, WO 93/12108, WO 93/12107, WO 94/17058 and WO 95106037 disclose imidazole derivatives having histamine H3 receptor agonistic or antagonistic activity. These derivatives have a five or six membered nitrogen containing ring attached to the 4-position of the imidazole ring and thus differ structurally from the present compounds which have a five or six membered carbocyclic ring optionally containing one or two double bonds in the same position.

WO 93/14070 disclose imidazole derivatives having histamine H3 antagonistic activity. These derivatives have a hydrocarbon chain optionally containing one or more heteroatoms attached to the 4-position of the imidazole ring which hydrocarbon chain may bear a cycloalkyl or cycloalkenyl group. U.S. Pat. No. 5,578,616 (corresponding to WO 95/14007) discloses phenyl-alkyl imidazoles as histamine H3 receptor antagonists. These phenyl-alkyl imidazoles differ structurally from the present compounds by having a $C_{1-3}$-alkylene group inserted between the imidazole ring and the phenyl ring. In the present compounds, on the contrary, the imidazole ring is directly attached to a five or six membered carbocyclic ring optionally containing one or two double bonds.

WO 96/40126 discloses substituted imidazole derivatives having histamine H3 receptor agonistic activity. Some of these may have a cyclohexyl group directly attached to the 4-position of the imidazole ring. However, a nitrogen atom is always attached to the 4-position of the cyclohexyl ring.

Furthermore, WO 98/07718 and Chemical Abstracts, Volume 84, No 11, Mar. 15, 1976, 73197p disclose imidazole derivatives. However, they are not disclosed as histamine H3 receptor agonists or antagonists.

In view of the arts' interest in histamine H3 receptor agonists and antagonists, novel compounds which trigger the histamine H3 receptor would be a highly desirable contribution to the art. The present invention provides such a contribution to the art being based on the finding that a novel class of substituted imidazole compounds has a high and specific affinity to the histamine H3 receptor and possesses histamine H3 receptor antagonistic activity.

Due to their histamine H3 receptor antagonistic activity the present compounds are useful in the treatment and/or prevention of a wide range of conditions and disorders in which a blockade of the histamine H3 receptor is beneficial. Thus, the compounds may find use, e.g., in the treatment of diseases of the central nervous system, the peripheral nervous system, the cardiovascular system, the pulmonary system, the gastrointestinal system and the endocrinologic system.

Definitions

In the structural formulas given herein and throughout the present specification, the following terms have the indicated meaning:

The term "$C_{1-6}$-alkyl" as used herein represents a branched or straight hydrocarbon group having from 1 to 6 carbon atoms. Typical $C_{1-6}$-alkyl groups include, but are not limited to, methyl, ethyl, n-propyl, isopropyl, butyl, isobutyl, sec-butyl, tert-butyl, pentyl, isopentyl, hexyl, isohexyl and the like.

The term "$C_{1-6}$-alkoxy" as used herein, alone or in combination, refers to the radical —O—$_{1-6}$-alkyl where $C_{1-6}$-alkyl is as defined above. Representative examples are methoxy, ethoxy, n-propoxy, isopropoxy, butoxy, sec-butoxy, tert-butoxy, pentoxy, isopentoxy, hexoxy, isohexoxy and the like.

The term "$C_{1-6}$-alkylsulfonyl" as used herein, alone or in combination, refers to the radical —S(=O)$_2$—$C_{1-6}$-alkyl where $C_{1-6}$-alkyl is as defined above. Representative examples are methylsulfonyl, ethylsulfonyl, n-propylsulfonyl, isopropylsulfonyl, butylsulfonyl, isobutylsulfonyl, sec-butylsulfonyl, tert-butylsulfonyl, pentylsulfonyl, isopentylsulfonyl, hexylsulfonyl, isohexylsulfonyl and the like.

The term "$C_{3-8}$-cycloalkyl" as used herein represents a carbocyclic group having from 3 to 8 carbon atoms. Representative examples are cyclopropyl, cyclobutyl, cyclopentyl, cyclohexyl, cycloheptyl, cyclooctyl, and the like.

The term "aryl" as used herein is intended to include carbocyclic aromatic ring systems such as phenyl, naphthyl (1-naphthyl or 2-naphthyl), anthracenyl (1-anthracenyl, 2-anthracenyl, 3-anthracenyl), phenanthrenyl, fluorenyl, indenyl and the like. Aryl is also intended to include the partially hydrogenated derivatives of the carbocyclic systems enumerated above. Non-limiting examples of such partially hydrogenated derivatives are 1-(1,2,3,4-tetrahydronaphthyl) and 2-(1,2,3,4-tetrahydronaphthyl).

The term "arylsulfonyl" as used herein refers to the radical —S(=O)$_2$-aryl where aryl is as defined above. Non-limiting examples are phenylsulfonyl, naphthylsulfonyl, phenanthrenylsulfonyl, fluorenylsulfonyl, indenylsulfonyl and the like.

The term "heteroaryl" as used herein is intended to include heterocyclic aromatic ring systems containing one or more heteroatoms selected from nitrogen, oxygen and sulfur, such as furyl, thienyl, pyrrolyl, oxazolyl, thiazolyl, imidazolyl, isoxazolyl, isothiazolyl, triazolyl, pyranyl, pyridyl, pyridazinyl, pyrimidinyl, pyrazinyl, triazinyl, thiadiazinyl, indolyl, isoindolyl, benzofuryl, benzothienyl, indazolyl, benzimidazolyl, benzthiazolyl, purinyl, quinazolinyl, quinolizinyl, quinolinyl, isoquinolinyl, quinoxalinyl, naphthyridinyl, pteridinyl, carbazolyl, acridinyl and the like. Heteroaryl is also intended to include the partially or fully hydrogenated derivatives of the heterocyclic systems enumerated above. Non-limiting examples of such partially or fully hydrogenated derivatives are pyrrolinyl, pyrazolinyl, indolinyl, pyrrolidinyl, piperidinyl, piperazinyl, azepinyl, diazepinyl, morpholinyl, thiomorpholinyl, oxazolidinyl, oxazolinyl, oxazepinyl, aziridinyl and tetrahydrofuranyl.

The term "halogen" means fluorine, chlorine, bromine or iodine.

As used herein, the phrase "3 to 8 membered, saturated or unsaturated, carbocyclic or heterocyclic ring" is intended to include carbocyclic rings which are saturated or contain one or more double bonds as well as heterocyclic rings containing one or more heteroatoms selected from nitrogen, oxygen or sulfur which are saturated or contain one or more double bonds.

The term "optionally substituted" as used herein means that the groups in question are either unsubstituted or substituted with one or more of the substituents specified. When the groups in question are substituted with more than one substituent the substituents may be the same or different.

As used herein, the phrase "a functional group which can be converted to hydrogen in vivo" is intended to include any group which upon administering the present compounds to the subjects in need thereof can be converted to hydrogen, e.g.,. enzymatically or by the acidic environment in the stomach. Non-limiting examples of such groups are acyl, carbamoyl, monoalkylated carbamoyl, dialkylated carbamoyl, alkoxycarbonyl, alkoxyalkyl groups and the like such as $C_{1-6}$-alkanoyl, aroyl, $C_{1-6}$-alkylcarbamoyl, di-$C_{1-6}$-alkylcarbamoyl, $C_{1-6}$-alkoxycarbonyl and $C_{1-6}$-alkoxy-$C_{1-6}$-alkyl.

Certain of the above defined terms may occur more than once in the structural formulas, and upon such occurrence each term shall be defined independently of the other.

DESCRIPTION OF THE INVENTION

The present invention relates to novel substituted imidazoles of formula I

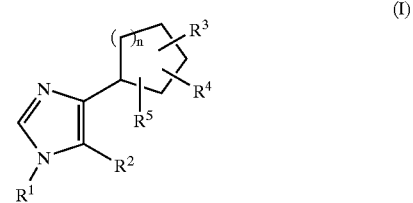

(I)

wherein the carbocyclic ring optionally contains one or two double bonds;

n represents 1 or 2;

$R^1$ is hydrogen or a functional group which can be converted to hydrogen in vivo;

$R^2$ is hydrogen, $C_{1-6}$-alkyl, cyano or halogen;

$R^3$ is hydrogen, hydroxy or halogen;

$R^4$ is hydrogen, hydroxy or cyano;

$R^5$ is hydrogen;

aryl optionally substituted with halogen, $C_{1-6}$-alkoxy, $C_{1-6}$-alkyl, trifluoromethyl, $C_{3-8}$-cycloalkyl, aryl or heteroaryl;

$C_{1-6}$-alkyl optionally substituted with $C_{3-8}$-cycloalkyl optionally substituted with halogen, $C_{1-6}$-alkoxy, $C_{1-6}$-alkyl, trifluoromethyl, $C_{3-8}$-cycloalkyl, aryl or heteroaryl;

aryl optionally substituted with halogen, $C_{1-6}$-alkoxy, $C_{1-6}$-alkyl, trifluoromethyl, $C_{3-8}$-cycloalkyl, aryl or heteroaryl; or heteroaryl optionally substituted with halogen, $C_{1-6}$-alkoxy, $C_{1-6}$-alkyl, trifluoromethyl, $C_{3-8}$-cycloalkyl, aryl or heteroaryl;

—X—$R^6$ wherein X is —O— or —S—; and $R^6$ is hydrogen;

$C_{1-6}$-alkyl optionally substituted with halogen, $C_{1-6}$-alkoxy, trifluoromethyl, $C_{3-8}$-cycloalkyl, aryl or heteroaryl where the $C_{3-8}$-cycloalkyl, aryl and heteroaryl groups optionally are substituted with halogen, $C_{1-6}$-alkoxy, $C_{1-6}$-alkyl, trifluoromethyl, $C_{3-8}$-cycloalkyl, aryl or heteroaryl;

$C_{3-8}$-cycloalkyl optionally substituted with halogen, $C_{1-6}$-alkoxy, $C_{1-6}$-alkyl, trifluoromethyl, $C_{3-8}$-cycloalkyl, aryl or heteroaryl;

aryl optionally substituted with halogen, $C_{1-6}$-alkoxy, $C_{1-6}$-alkyl, trifluoromethyl, $C_{3-8}$-cycloalkyl, aryl or heteroaryl;

heteroaryl optionally substituted with halogen, $C_{1-6}$-alkoxy, $C_{1-6}$-alkyl, trifluoromethyl, $C_{3-8}$-cycloalkyl, aryl or heteroaryl;

—CONR$^7$R$^8$ wherein $R^7$ and $R^8$ independently are hydrogen;

$C_{1-6}$-alkyl optionally substituted with halogen, $C_{1-6}$-alkoxy, trifluoromethyl, $C_{3-8}$-cycloalkyl, aryl or heteroaryl where the $C_{3-8}$-cycloalkyl, aryl and heteroaryl groups optionally are substituted with halogen, $C_{1-6}$-alkoxy, $C_{1-6}$-alkyl, trifluoromethyl, $C_{3-8}$-cycloalkyl, aryl or heteroaryl;

$C_{3-8}$-cycloalkyl optionally substituted with halogen, $C_{1-6}$-alkoxy, $C_{1-6}$-alkyl, trifluoromethyl, $C_{3-8}$-cycloalkyl, aryl or heteroaryl;

aryl optionally substituted with halogen, $C_{1-6}$-alkoxy, $C_{1-6}$-alkyl, trifluoromethyl, $C_{3-8}$-cycloalkyl, aryl or heteroaryl;

heteroaryl optionally substituted with halogen, $C_{1-6}$-alkoxy, $C_{1-6}$-alkyl, trifluoromethyl, $C_{3-8}$-cycloalkyl, aryl or heteroaryl; or $R^7$ and $R^8$ together form a 3 to 8 membered, saturated or unsaturated carbocyclic or heterocyclic ring which is optionally substituted with halogen, $C_{1-6}$-alkoxy, $C_{1-6}$-alkyl, trifluoromethyl, $C_{3-8}$-cycloalkyl, aryl or heteroaryl; or —$SO_2R^7$ wherein $R^7$ is as defined above;

with the proviso that when X is —S—; $R^6$ must not be hydrogen, —$CONR^7R^8$ or —$SO_2R^7$; or —$CONR^7R^8$ wherein $R^7$ and $R^8$ are as defined above; or $R^4$ and $R^5$ taken together represent =O;

with the provisos that when $R^2$ is hydrogen; $R^3$, $R^4$ or $R^5$ must not be methyl or ethyl in the 1 position;

when n is 2; $R^1$ is —$CPh_3$; $R^2$ and $R^3$ are hydrogen; $R^4$ is cyano in the 1 position; $R^5$ must not be hydrogen;

when n is 2; $R^1$, $R^2$, $R^3$ and $R^4$ are hydrogen; $R^5$ must not be hydrogen;

as well as any optical or geometric isomer or tautomeric form thereof including mixtures of these or a pharmaceutically acceptable salt thereof.

In a preferred embodiment the invention relates to compounds of the formula I wherein n is 2.

In another preferred embodiment of the invention the carbocyclic ring is cyclohexyl.

In still another preferred embodiment the invention relates to compounds of the formula I wherein $R^1$ and $R^2$ are both hydrogen.

A further preferred embodiment of the invention relates to compounds of the formula I wherein $R^3$ and $R^4$ are both hydrogen.

A further preferred embodiment of the invention relates to compounds of the formula I wherein $R^5$ is —X—$R^6$ and n, the carbocyclic ring, $R^1$, $R^2$, $R^3$ and $R^4$ are as defined for formula I and preferably as defined in the preferred embodiments above.

$R^6$ is preferably hydrogen; $C_{1-6}$-alkyl optionally substituted as defined for formula I; aryl optionally substituted as defined for formula I; or —$CONR^7R^8$ wherein $R^7$ and $R^8$ are as defined for formula I.

A particularly preferred group of the compounds of the formula I as defined above are such compounds wherein wherein X is —O— and $R^6$ is $C_{1-6}$-alkyl substituted with phenyl which is optionally substituted with halogen, cyano or trifluoromethyl; phenyl optionally substituted with halogen, cyano or trifluoromethyl; or —$CONR^7R^8$ wherein $R^7$ and $R^8$ independently are hydrogen; $C_{1-6}$-alkyl substituted with phenyl which is optionally substituted with halogen, cyano or trifluoromethyl; or phenyl optionally substituted with halogen, cyano or trifluoromethyl. Preferably, one of $R^7$ and $R^8$ represents hydrogen while the other represents one of the other groups mentioned.

The above ethers offer the advantages of being stable towards hydrolytic cleavage and of being lipophilic which indicates a good blood-brain-barrier penetration.

The compounds of the present invention may have one or more asymmetric centers and it is intended that any optical isomers, as separated, pure or partially purified optical isomers or racemic mixtures thereof are included within the scope of the invention.

Furthermore, geometric isomers may be formed. It is intended that any geometric isomers, as separated, pure or partially purified geometric isomers or mixtures thereof are included within the scope of the invention. Likewise, molecules having a bond with restricted rotation may form geometric isomers. These are also intended to be included within the scope of the present invention.

Furthermore, the compounds of the present invention may exist in different tautomeric forms and it is intended that any tautomeric forms which the compounds are able to form are included within the scope of the present invention.

The present invention also encompasses pharmaceutically acceptable salts of the present compounds. Such salts include pharmaceutically acceptable acid addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric acids and the like. Further examples of pharmaceutically acceptable inorganic or organic acid addition salts include the pharmaceutically acceptable salts listed in *J. Pharm. Sci.* 1977, 66, 2, which is incorporated herein by reference. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like.

Also intended as pharmaceutically acceptable acid addition salts are the hydrates which the present compounds are able to form.

The acid addition salts may be obtained as the direct products of compound synthesis. In the alternative, the free base may be dissolved in a suitable solvent containing the appropriate acid, and the salt isolated by evaporating the solvent or otherwise separating the salt and solvent.

The compounds of the present invention may form solvates with standard low molecular weight solvents using methods known to the skilled artisan. Such solvates are also contemplated as being within the scope of the present invention.

The invention also encompasses prodrugs of the present compounds which on administration undergo chemical conversion by metabolic processes before becoming active pharmacological substances. In general, such prodrugs will be functional derivatives of the compounds which are readily convertible in vivo into the present compounds. Conventional procedures for the selection and preparation of suitable prodrug derivatives are described, for example, in "Design of Prodrugs", ed. H. Bundgaard, Elsevier, 1985.

The invention also encompasses active metabolites of the present compounds.

The compounds of the present invention interact with the histamine H3 receptor and may thus be used for the treatment of a wide range of disorders related to the histamine H3 receptor.

Accordingly, in another aspect the present invention relates to a compound of formula I or any optical or geometric isomer or tautomeric form thereof including mixtures of these or a pharmaceutically acceptable salt thereof for use as a medicament.

The invention also relates to pharmaceutical compositions comprising, as an active ingredient, at least one compound of the formula I or any optical or geometric isomer or tautomeric form thereof including mixtures of these or a pharmaceutically acceptable salt thereof together with one or more pharmaceutically acceptable carriers or diluents.

Furthermore, the invention relates to the use of a compound of formula I or any optical or geometric isomer or tautomeric form thereof including mixtures of these or a pharmaceutically acceptable salt thereof for the preparation of a medicament for the treatment of disorders related to the histamine H3 receptor.

In still another aspect, the invention relates to a method for the treatment of disorders related to the histamine H3 receptor, the method comprising administering to a subject in need thereof an effective amount of a compound of formula I or any optical or geometric isomer or tautomeric form thereof including mixtures of these or a pharmaceutically acceptable salt thereof or a pharmaceutical composition comprising the same.

More particularly, the present compounds possess histamine H3 receptor antagonistic activity and are accordingly useful in the treatment of a wide range of conditions and disorders in which a histamine H3 receptor blockade is beneficial.

The compounds of the present invention may thus be used for the treatment of airway disorders such as asthma, as anti-diarrheals and for the modulation of gastric acid secretion.

The compounds of the present invention may also be used for the treatment of diseases associated with the regulation of sleep and wakefulness and for the treatment of narcolepsy and attention deficit disorders.

Moreover, the compounds of the invention may be used as stimulants or as sedatives.

The compounds of the invention may also be useful for the treatment of eating disorders such as binge eating or bulimia by virtue of their appetite regulating properties.

Furthermore, the present compounds may be useful for the treatment and/or prevention of obesity as well as diseases related to obesity, such as diabetes and cardiovascular disorders.

The present compounds may also be used for the treatment of conditions associated with epilepsy. Additionally, the present compounds may be used for the treatment of motion sickness and vertigo. Furthermore, they may be useful as regulators of hypothalamo-hypophyseal secretion, antidepressants, modulators of cerebral circulation, and in the treatment of irritable bowel syndrome.

Further, the compounds of the present invention may be used for the treatment of dementia and Alzheimer's disease. Moreover, the compounds of the present invention may be used as analgetics and for the treatment of inflammatory painful conditions or neurogenic inflammation.

The present novel compounds may also interact with the vanilloid receptors, the serotonin receptors, and the adrenergic receptors and may be useful for the treatment of diseases associated with these receptors. Hence, the compounds of the present invention may be vanilloid receptor agonists, and thus be useful for the treatment of obesity by enhancement of the metabolic rate and energy expenditure. Further, by virtue of their interaction with the vanilloid receptor the compounds of the present invention may be useful for the treatment of pain or neurogenic inflammation or inflammatory painful conditions.

Furthermore, by virtue of their interaction with the 5-HT3 receptor (serotonin-3-receptor), the compounds of the present invention may be useful as antiemetics, in particular the chemotherapy-induced emesis. Further potential applications of 5-HT3 antagonists include treatment of central nervous system disorders such as anxiety, schizophrenia, drug abuse and withdrawal symptoms, and pathological and age-associated amnesia.

Furthermore, the present compounds may be alpha-2-adrenoceptor agonists or antagonists and thus be useful for the treatment of hypertension and of conditions associated with overexpression or hypersensitization of adrenergic alpha-2 receptors, especially obesity, withdrawal symptoms to an adrenergic alpha-2 agonist, neurological disorders (especially orthostatic hypotension), multiple system atrophy, diabetes mellitus, benign prostatic hyperplasia or drug induced sensitization of adrenergic alpha-2 receptors. Moreover, the compounds of the present invention, by virtue of their interaction with alpha-2 receptors, may be useful as sedatives and hypnotics (sleep inducing agents) or as stimulants.

In a preferred embodiment of the invention the present compounds are used for the preparation of a medicament for the reduction of weight.

In a preferred embodiment of the invention the present compounds are used for the preparation of a medicament for the treatment and/or prevention of overweight or obesity.

In another preferred embodiment of the invention the present compounds are used for the preparation of a medicament for the suppression of appetite or satiety induction.

In a further preferred embodiment of the invention the present compounds are used for the preparation of a medicament for the prevention and/or treatment of disorders and diseases related to overweight or obesity such as atherosclerosis, hypertension, diabetes, especially Type 2 diabetes (NIDDM (non-insulin dependent diabetes mellitus)), dyslipidemia, coronary heart disease, gallbladder disease, osteoarthritis and various types of cancer such as endometrial, breast, prostate and colon cancers.

In yet a further preferred embodiment of the invention the present compounds are used for the preparation of a medicament for the prevention and/or treatment of eating disorders such as bulimia and binge eating.

In a further aspect of the invention the present compounds may be administered in combination with one or more further pharmacologically active substances, e.g., other anti-obesity agents or appetite regulating agents.

Such agents may be selected from the group consisting of CART agonists, NPY antagonists, MC4 agonists, orexin antagonists, TNF agonists, CRF agonists, CRF BP antagonists, urocortin agonists, β3 agonists, MSH (melanocyte-stimulating hormone) agonists, MCH (melanocyte-concentrating hormone) antagonists, CCK agonists, serotonin re-uptake inhibitors, mixed serotonin and noradrenergic compounds, 5HT agonists, bombesin agonists, galanin antagonists, growth hormone, growth hormone releasing compounds, TRH agonists, uncoupling protein 2 or 3 modulators, GLP-1, leptin agonists, DA agonists (bromocriptin, doprexin), lipase/amylase inhibitors, PPAR modulators, RXR modulators or TR β agonists.

In a preferred embodiment of the invention the antiobesity agent is leptin.

In another preferred embodiment the antiobesity agent is dexamphetamine or amphetamine.

In another preferred embodiment the antiobesity agent is fenfluramine or dexfenfluramine.

In still another preferred embodiment the antiobesity agent is sibutramine.

In a further preferred embodiment the antiobesity agent is orlistat.

In another preferred embodiment the antiobesity agent is mazindol or phentermine.

The present compounds may also be administered in combination with one or more antidiabetics or other pharmacologically active material(s), including compounds for the treatment and/or prophylaxis of insulin resistance and diseases, wherein insulin resistance is the pathophysiological mechanism. Suitable antidiabetics comprise insulin, GLP-1 derivatives such as those disclosed in WO 98/08871 to Novo Nordisk A/S, which is incorporated herein by reference, as well as orally active hypoglycemic agents.

The orally active hypoglycemic agents preferably comprise sulphonylureas, biguanides, meglitinides, oxadiazolidinediones, thiazolidinediones, glucosidase inhibitors, glucagon antagonists such as those disclosed in WO 99/01423 to Novo Nordisk A/S and Agouron Pharmaceuticals, Inc., GLP-1 agonists, potassium channel openers such as those disclosed in WO 97/26265 and WO 99/03861 to Novo Nordisk A/S which are incorporated herein by reference, insulin sensitizers Furthermore, the present compounds may be administered in combination with the insulin sensitizers such as those disclosed in WO 99/19313 to Dr. Reddy's Research Foundation, DPP-IV inhibitors, inhibitors of hepatic enzymes involved in stimulation of gluconeogenesis and/or glycogenolysis, glucose uptake modulators, compounds modifying the lipid metabolism such as antihyperlipidemic agents and antilipidemic agents, compounds lowering food intake, PPAR and RXR agonists and agents acting on the ATP-dependent potassium channel of the β-cells.

In a preferred embodiment of the invention the present compounds are administered in combination with insulin.

In a further preferred embodiment the present compounds are administered in combination with a sulphonylurea, e.g., tolbutamide, glibenclamide, glipizide or glicazide.

In another preferred embodiment the present compounds are administered in combination with a biguanide, e.g., mefformin.

In yet another embodiment the present compounds are administered in combination with a meglitinide, e.g., repaglinide.

In still another preferred embodiment the present compounds are administered in combination with a thiazolidinedione selected from troglitazone, ciglitazone, pioglitazone, rosiglitazone and the compounds disclosed in WO 97/41097 to Dr. Reddy's Research Foundation, especially 5-[[4-[(3,4-dihydro-3-methyl-4-oxo-2-quinazolinylmethoxy]phenyl]-methyl]-2,4-thiazolidinedione.

In a further preferred embodiment the present compounds are administered in combination with an a-glucosidase inhibitor, e.g., miglitol or acarbose.

In yet a preferred embodiment the present compounds are administered in combination with an agent acting on the ATP-dependent potassium channel of the β-cells selected from tolbutamide, glibenclamide, glipizide, glicazide and repaglinide.

Furthermore, the present compounds may be administered in combination with nateglinide.

In still another embodiment the present compounds are administered in combination with an antihyperlipidemic agent or antilipidemic agent, e.g., cholestyramine, colestipol, clofibrate, gemfibrozil, lovastatin, pravastatin, simvastatin, probucol or dextrothyroxine.

In a further embodiment the present compounds are administered in combination with more than one of the above-mentioned compounds, e.g., in combination with a sulphonylurea and metformin, a sulphonylurea and acarbose, repaglinide and metformin, insulin and a sulphonylurea, insulin and metformin, insulin and troglitazone, insulin and lovastatin, etc.

Furthermore, the present compounds may be administered in combination with one or more antihypertensive agents. Examples of antihypertensive agents are β-blockers such as alprenolol, atenolol, timolol, pindolol, propranolol and metoprolol, ACE (angiotensin converting enzyme) inhibitors such as benazepril, captopril, enalapril, fosinopril, lisinopril, quinapril and ramipril, calcium channel blockers such as nifedipine, felodipine, nicardipine, isradipine, nimodipine, diltiazem and verapamil, and α-blockers such as doxazosin, urapidil, prazosin and terazosin. Further reference can be made to Remington: The Science and Practice of Pharmacy, 19$^{th}$ Edition, Gennaro, Ed., Mack Publishing Co., Easton, Pa., 1995.

It should be understood that any suitable combination of the compounds according to the invention with one or more of the above-mentioned compounds and optionally one or more further pharmacologically active substances are considered to be within the scope of the present invention.

Pharmaceutical Compositions

The compounds of the invention may be administered alone or in combination with pharmaceutically acceptable carriers or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as the oral, rectal, nasal, pulmonary, topical (including buccal and sublingual), transdermal, intracisternal, intraperitoneal, vaginal and parenteral (including subcutaneous, intramuscular, intrathecal, intravenous and intradermal) route, the oral route being preferred. It will be appreciated that the preferred route will depend on the general condition and age of the subject to be treated, the nature of the condition to be treated and the active ingredient chosen.

Pharmaceutical compositions for oral administration include solid dosage forms such as capsules, tablets, dragees, pills, lozenges, powders and granules. Where appropriate, they can be prepared with coatings such as enteric coatings or they can be formulated so as to provide controlled release of the active ingredient such as sustained or prolonged release according to methods well-known in the art.

Liquid dosage forms for oral administration include solutions, emulsions, suspensions, syrups and elixirs.

Pharmaceutical compositions for parenteral administration include sterile aqueous and non-aqueous injectable solutions, dispersions, suspensions or emulsions as well as sterile powders to be reconstituted in sterile injectable solutions or dispersions prior to use. Depot injectable formulations are also contemplated as being within the scope of the present invention.

Other suitable administration forms include suppositories, sprays, ointments, cremes, gels, inhalants, dermal patches, implants etc.

A typical oral dosage is in the range of from about 0.001 to about 100 mg/kg body weight per day, preferably from about 0.01 to about 50 mg/kg body weight per day, and more preferred from about 0.05 to about 10 mg/kg body weight per day administered in one or more dosages such as 1 to 3 dosages. The exact dosage will depend upon the frequency and mode of administration, the sex, age, weight and general condition of the subject treated, the nature and severity of the condition treated and any concomitant diseases to be treated and other factors evident to those skilled in the art.

The formulations may conveniently be presented in unit dosage form by methods known to those skilled in the art. A typical unit dosage form for oral administration one or more times per day such as 1 to 3 times per day may contain of from 0.05 to about 1000 mg, preferably from about 0.1 to about 500 mg, and more preferred from about 0.5 mg to about 200 mg.

For parenteral routes, such as intravenous, intrathecal, intramuscular and similar administration, typically doses are in the order of about half the dose employed for oral administration.

The compounds of this invention are generally utilized as the free substance or as a pharmaceutically acceptable salt thereof. One example is an acid addition salt of a compound having the utility of a free base. When a compound according to the invention contains a free base such salts are prepared in a conventional manner by treating a solution or suspension of a free base of the compound according to the invention with a chemical equivalent of a pharmaceutically acceptable acid, for example, inorganic and organic acids. Representative examples are mentioned above. Physiologically acceptable salts of a compound with a hydroxy group include the anion of said compound in combination with a suitable cation such as sodium or ammonium ion.

For parenteral administration, solutions of the present compounds in sterile aqueous solution, aqueous propylene glycol or sesame or peanut oil may be employed. Such aqueous solutions should be suitable buffered if necessary and the liquid diluent first rendered isotonic with sufficient saline or glucose. The aqueous solutions are particularly suitable for intravenous, intramuscular, subcutaneous and intraperitoneal administration. The sterile aqueous media employed are all readily available by standard techniques known to those skilled in the art.

Suitable pharmaceutical carriers include inert solid diluents or fillers, sterile aqueous solution and various organic solvents. Examples of solid carriers are lactose, terra alba, sucrose, cyclodextrin, talc, gelatine, agar, pectin, acacia, magnesium stearate, stearic acid or lower alkyl ethers of cellulose. Examples of liquid carriers are syrup, peanut oil, olive oil, phospholipids, fatty acids, fatty acid amines, polyoxyethylene or water. Similarly, the carrier or diluent may include any sustained release material known in the art, such as glyceryl monostearate or glyceryl distearate, alone or mixed with a wax. The pharmaceutical compositions formed by combining the compounds according to the invention and the pharmaceutically acceptable carriers are then readily administered in a variety of dosage forms suitable for the disclosed routes of administration. The formulations may conveniently be presented in unit dosage form by methods known in the art of pharmacy.

Formulations of the present invention suitable for oral administration may be presented as discrete units such as capsules or tablets, each containing a predetermined amount of the active ingredient, and which may include a suitable excipient. These formulations may be in the form of powder or granules, as a solution or suspension in an aqueous or non-aqueous liquid, or as an oil-in-water or water-in-oil liquid emulsion.

If a solid carrier is used for oral administration, the preparation may be tabletted, placed in a hard gelatin capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

A typical tablet which may be prepared by conventional tabletting techniques may contain:

| Core: | |
| --- | --- |
| Active compound (as free compound or salt thereof) | 5.0 mg |
| Lactosum Ph. Eur. | 67.8 mg |
| Cellulose, microcryst. (AVICEL) | 31.4 mg |
| AMBERLITE | 1.0 mg |
| Magnesii stearas Ph. Eur. | q.s. |
| Coating: | |
| HPMC approx. | 9 mg |
| Mywacett 9-40 T* approx. | 0.9 mg |

*Acylated monoglyceride used as plasticizer for film coating.

If desired, the pharmaceutical composition of the invention may comprise the compound of the formula I in combination with one or more other pharmacologically active substances.

The preparation of the compounds according to the invention can be realized in many ways.

The synthesis of compounds of formula I, wherein the carbocyclic ring is a six membered carbocyclic ring (Ia, saturated ring; Ib, the ring contains one double bond; Ic, the ring contains two double bonds) ($R^1$ and $R^2$ are as defined for formula I, $R^3$=$R^4$=H, $R^5$=—O—$R^6$, wherein $R^6$ is as defined for formula I) is sketched below:

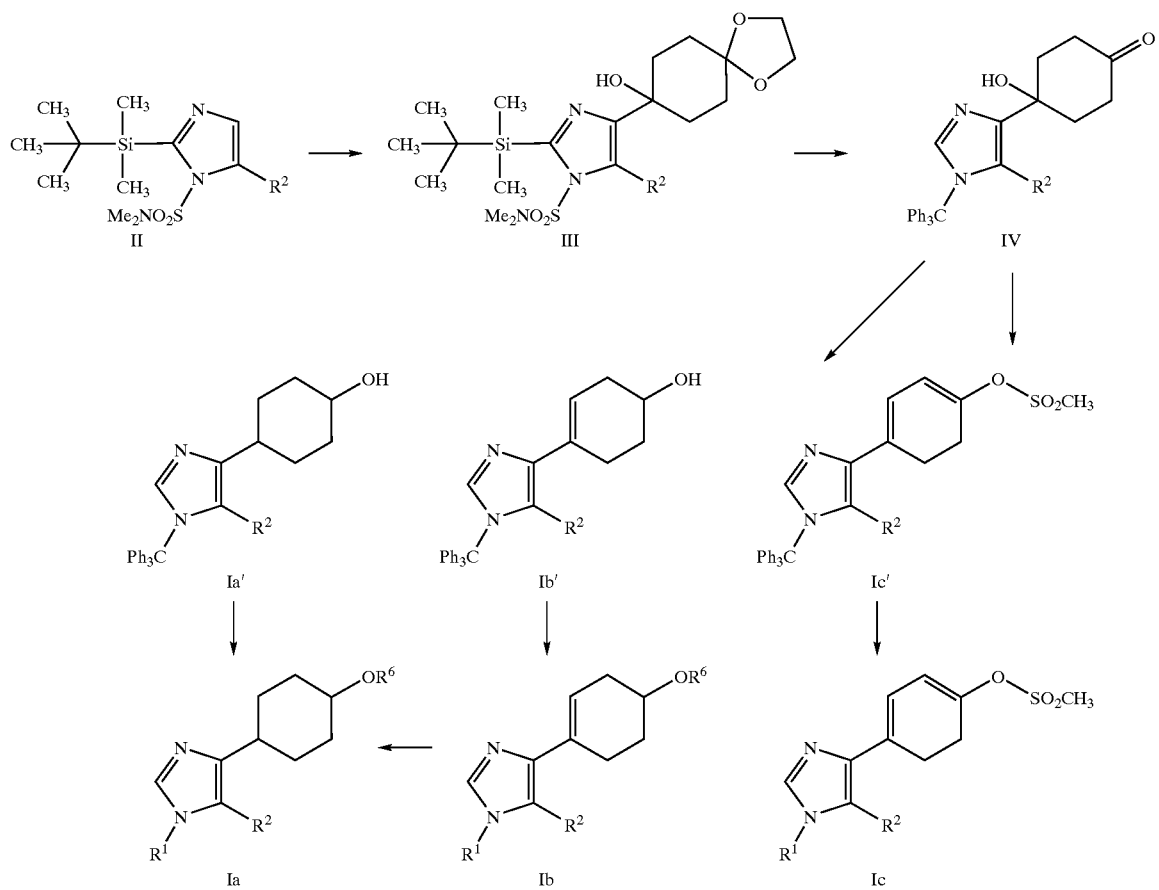

In this synthesis 1-(dimethylaminosulfonyl)-2-(dimethyl-tert-butylsilyl)imidazoles II (R. Ganellin et al., *J. Med. Chem.* 1996, 39, 3806–3813) are lithiated and then reacted with cyclohexane-1,4-dione monoethyleneketal to give tertiary alcohols III. Other, similarly protected imidazole derivatives may alternatively be used. Acidolytic removal of the protecting groups followed by tritylation yields keto-alcohols IV. These alcohols IV can be used for the preparation of the compounds of formulas Ia, Ib or Ic which form part of the present compounds of formula I.

Thus, treatment of the keto-alcohols IV with methanesulfonyl chloride and triethylamine leads to elimination of water with simultaneous formation of products of formula Ic'. Acidolytic removal of the protecting group and optional introduction of the group $R^1$ leads to the formation of products Ic wherein $R^6$ is —$SO_2CH_3$.

Reduction of the products resulting from elimination of water with a reducing agent such as sodium borohydride leads to the formation of alcohols Ib', which can be used as starting materials for the preparation of compounds of formulas Ia' and Ib.

Compounds of formula Ia' can be prepared by hydrogenation of Ib'.

Compounds of formula Ib can be prepared by chemical transformation of the hydroxy group in the alcohols Ib' into a group —$OR^6$ and conversion of the trityl group into the group $R^1$.

Conversion of the alcohols Ia' into compounds of formula Ia is analogous to the conversion of Ib' into Ib.

Alternatively, compounds Ia may be prepared by hydrogenation of Ib, if the groups $R^1$ and $R^6$ are stable towards the hydrogenation conditions.

The conversion of the hydroxy group of Ia' or Ib' into the group —$OR^6$ can be achieved using conventional synthetic methodology. For instance, alkylation of the hydroxy group of alcohols Ia' or Ib' with alkyl halides or alkyl sulfonic esters (Williamson ether synthesis) yields alkyl ethers ($R^6$= primary or secondary substituted or unsubstituted alkyl). Mitsunobu etherification can be used for the preparation of arylethers ($R^6$=substituted or unsubstituted aryl). Reaction of the alcohols Ia' or Ib' with isocyanates or carbamoyl chlorides yields carbamates (urethanes) ($R^6$=—$CONR^7R^8$ wherein $R^7$ and $R^8$ are as defined for formula I). Conversion of the trityl group into a group $R^1$ can be realized by acid catalyzed detritylation (Tr→H), optionally followed by introduction of a chemically labile group $R^1$, such as an acyl group or a carbamoyl group, by conventional methods.

In yet another aspect, the present invention relates to a process for the preparation of a compound of formula Id

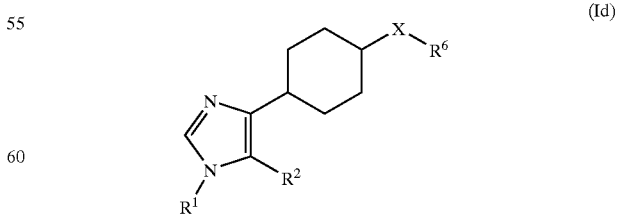

(Id)

wherein X, $R^1$, $R^2$ and $R^6$ are as defined for formula I, as well as any optical or geometric isomer or tautomeric form thereof including mixtures of these or a pharmaceutically acceptable salt thereof comprising the steps of reducing a 4-(4-oxocyclohex-1-enyl)imidazole derivative of the formula V

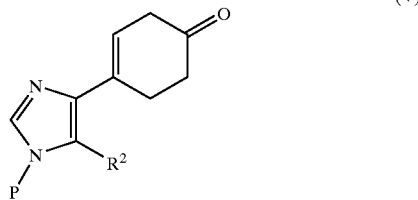

wherein P is an appropriate protecting group such as trityl, with a suitable reducing agent such as sodium borohydride to give a 4-(4-hydroxycyclohex-1-enyl) imidazole derivative of the formula Ib'

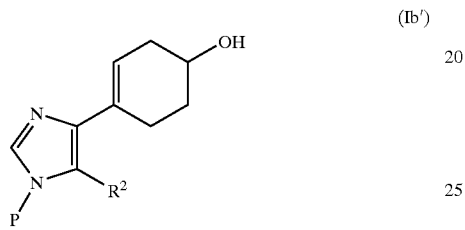

wherein P and $R^2$ are as defined above,
hydrogenating said derivative of the formula Ib' with a suitable hydrogenating agent such as hydrogen and a catalyst such as platinum to give a 4-(4-hydroxycyclohexyl)imidazole derivative of the formula Ia'

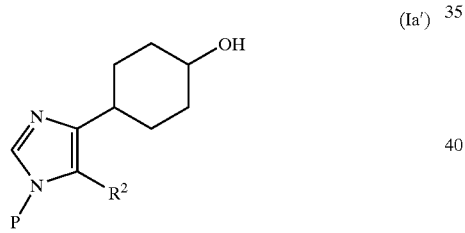

wherein P and $R^2$ are as defined above, and then
i) when X is oxygen and $R^6$ is hydrogen: deprotecting the derivative of the formula Ia' to give a compound of formula Id wherein $R^1$ is hydrogen and, if necessary, introducing a labile functional group to give a compound of formula Id wherein $R^1$ is a functional group which can be converted to hydrogen in vivo, and, if appropriate, separating the compound of formula Id into its diastereomeric or enantiomeric forms and, if desired, converting the compound of formula Id into a salt with a pharmaceutically acceptable acid,
ii) when X is oxygen and $R^6$ is $C_{1-6}$-alkyl, $C_{3-8}$cycloalkyl, aryl or heteroaryl which are optionally substituted as defined for formula I: etherifying said derivative of formula Ia' with $R^6$-Hal wherein $R^6$ has the above meanings and Hal represents halogen and deprotecting the resulting derivative to give a compound of formula Id wherein $R^1$ is hydrogen and, if necessary, introducing a labile functional group to give a compound of formula Id wherein $R^1$ is a functional group which can be converted to hydrogen in vivo, and, if appropriate, separating the compound of formula Id into its diastereomeric or enantiomeric forms and, if desired, converting the compound of formula Id into a salt with a pharmaceutically acceptable acid,
iii) when X is oxygen and $R^6$ is —$CONR^7R^8$ wherein $R^7$ and $R^8$ are as defined for formula I: reacting the derivative of formula Ia' with Cl—CO—$NR^7R^8$ or O=C=N—$R^7$ wherein $R^7$ and $R^8$ have the above meaning and deprotecting the resulting derivative to give a compound of formula Id wherein $R^1$ is hydrogen and, if necessary, introducing a labile functional group to give a compound of formula Id wherein $R^1$ is a functional group which can be converted to hydrogen in vivo, and, if appropriate, separating the compound of formula Id into its diastereomeric or enantiomeric forms and, if desired, converting the compound of formula Id into a salt with a pharmaceutically acceptable acid,
iv) when X is oxygen and $R^6$ is —$SO_2R^7$ wherein $R^7$ is as defined for formula I: reacting the derivative of formula Ia' with Cl—$SO_2$—$R^7$ wherein $R^7$ has the above meaning and deprotecting the resulting derivative to give a compound of formula Id wherein $R^1$ is hydrogen and, if necessary, introducing a labile functional group to give a compound of formula Id wherein $R^1$ is a functional group which can be converted to hydrogen in vivo, and, if appropriate, separating the compound of formula Id into its diastereomeric or enantiomeric forms and, if desired, converting the compound of formula Id into a salt with a pharmaceutically acceptable acid,
v) when X is sulfur and $R^6$ is $C_{1-6}$-alkyl, $C_{3-8}$-cycloalkyl, aryl or heteroaryl which are optionally substituted as defined for formula I: substituting the hydroxy group by $R^6$—SH wherein $R^6$ has the above meanings and deprotecting the resulting derivative to give a compound of formula Id wherein $R^1$ is hydrogen and, if necessary, introducing a labile functional group to give a compound of formula Id wherein $R^1$ is a functional group which can be converted to hydrogen in vivo, and, if appropriate, separating the compound of formula Id into its diastereomeric or enantiomeric forms and, if desired, converting the compound of formula Id into a salt with a pharmaceutically acceptable acid.

Compounds of formula Id wherein X is oxygen and $R^6$ is aryl or heteroaryl which are optionally substituted as defined for formula I may alternatively be prepared by nucleophilic substitution of the hydroxy group of the compounds of formula Ia' by the corresponding aromatic alcohols and heteroaromatic alcohols, respectively.

The starting compound of formula V may be obtained by the treatment of the compound of formula IV with methanesulfonyl chloride and triethylamine to eliminate water as explained above in connection with the general reaction scheme.

The present invention is further illustrated by the following representative examples, which are, however, not intended to limit the scope of the invention in any way.

EXAMPLES

In the examples the following terms are intended to have the following, general meanings:

DMSO: dimethyl sulfoxide
THF: tetrahydrofuran
m.p.: melting point

NMR spectra were recorded on Bruker 300 MHz and 400 MHz instruments. HPLC-MS was performed on a Perkin Elmer instrument (API 100), and HPLC-systems from Merck-Hitachi (Hibar™ RT 250-4, Lichrosorb™ RP 18, 5.0 μm, 4.0×250 mm, gradient elution, 20% to 80% acetonitrile in water within 30 min, 1.0 mL/min, detection at 254 nm) and Waters (Symmetry™, $C_{18}$, 3.5 μm, 3.0×150 mm, gradient elution, 5% to 90% acetonitrile in water within 15 min, 1.0 mL/min, detection at 214 nm) were used.

Example 1

Preparation of Intermediate 1

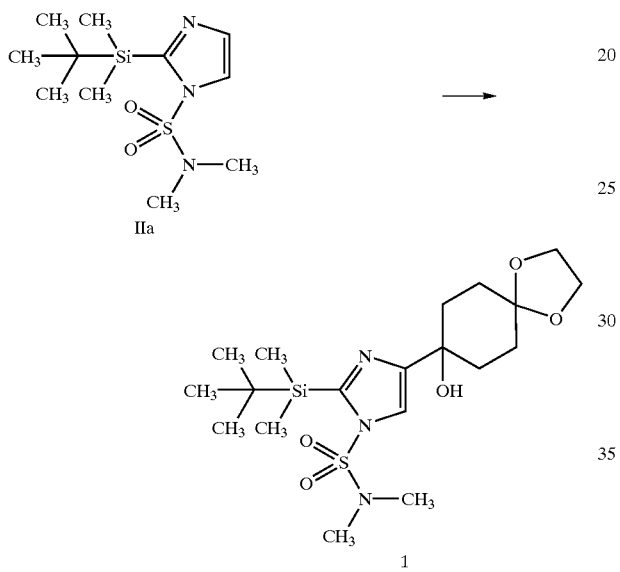

To a solution of compound IIa (9.26 g, 32.0 mmol) in dry THF (80 mL) at −78° C. butyllithium (22 mL of a 1.6 molar solution in hexanes, 35.2 mmol) was dropwise added. When the addition was finished the resulting mixture was stirred at −78° C. for 30 min, and then a solution of cyclohexane-1,4-dione monoethylene ketal (5.0 g, 32.0 mmol) in THF (20 mL) was added. The reaction mixture was then diluted with additional THF (50 mL) and allowed to warm to room temperature. After 1 h first a mixture of THF (20 mL) and ethanol (3 mL) and then water (50 mL) were carefully added. Extraction of the resulting mixture with ethyl acetate (2×50 mL), washing of the combined organic phases with brine (50 mL), drying (MgSO₄) and concentration yielded 14.5 g of an oil, which solidified within 16 h. Recrystallization (heptane/ethyl acetate) yielded 8.36 g (59%) of the alcohol 1 as a colorless solid, m.p. 89–91° C.

$^1$H NMR (300 MHz, DMSO-$d_6$): δ0.31 (s, 6H), 0.98 (s, 9H), 1.54 (m, 2H), 1.88 (m, 4H), 2.11 (m, 2H), 2.81 (s, 6H), 3.85 (s, 4H), 4.92 (s, 1H), 7.10 (s, 1H); $^{13}$C NMR (75 MHz, DMSO-$d_6$): δ0.00, 21.64, 30.42, 33.13, 37.89, 40.70, 66.61, 66.72, 70.80, 110.62, 132.66, 144.37, 160.12. Anal. Calcd. for $C_{19}H_{35}N_3O_5SSi$ (445.7): C, 51.21; H, 7.92; N, 9.43. Found: C, 51.55; H, 7.97; N, 9.46.

Upon concentration of the mother liquor more product (1.18 g, 8%) was obtained.

Example 2

Preparation of Intermediate 2

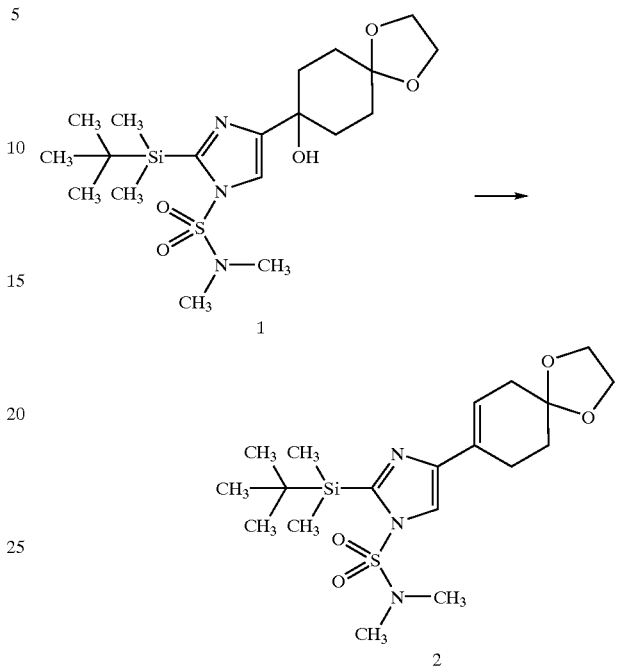

To a solution of the alcohol 1 (4.46 g, 10.0 mmol) and triethylamine (8.32 mL) in dichloromethane (30 mL) at 0° C. methanesulfonyl chloride (2.23 mL, 30 mmol) was dropwise added. After 1 h at room temperature more triethylamine (8.32 mL) and methanesulfonyl chloride (2.32 mL) were added and after stirring for one additional hour at room temperature water (100 mL) and dichloromethane (100 mL) were added. The phases were separated and the organic layer was washed with water (50 mL) and dried over MgSO₄ overnight. Concentration of the dried organic phase yielded 5.37 g of the crude, unstable compound of formula 2 as an oil.

$^1$H NMR (300 MHz, DMSO-$d_6$): δ0.31 (s, 6H), 1.02 (s, 9H), 1.78 (t, J=7 Hz, 2H), 2.36 (m, 2H), 2.42 (m, 2H), 2.74 (s, 6H), 3.92 (s, 4H), 5.78 (m, 1H), 6.98 (s, 1H).

Example 3

Preparation of Intermediate 3

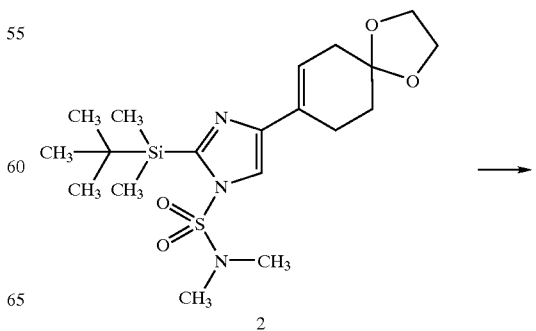

-continued

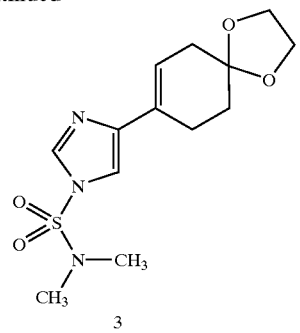

3

To a stirred suspension of silica gel (48 g) in dichloromethane (300 mL) first 15% aqueous sulfuric acid (4.8 mL) and then a solution of compound 2 (5.37 g, crude product) in dichloromethane (10 mL) were added. The resulting mixture was stirred at room temperature overnight, filtered, the silica gel washed with a mixture of dichloromethane and methanol (25:1, 450 mL), and the combined filtrates were concentrated. 3.20 g of compound 3 was obtained as an oil.

$^1$H NMR (300 MHz, DMSO-$d_6$): δ1.78 (t, J=7 Hz, 2H), 2.38 (m, 2H), 2.45 (m, 2H), 2.80 (s, 6H), 3.94 (s, 4H), 5.86 (m, 1H), 6.95 (s, 1H), 8.10 (s, 1H).

Example 4
Preparation of Intermediate 4

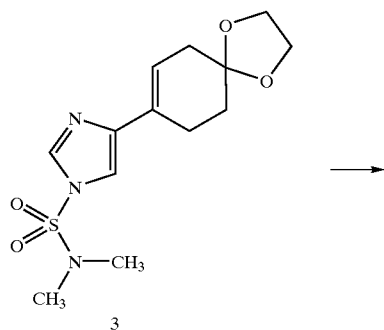

A mixture of the crude ketal 3 (3.20 g, approx. 10 mmol), silica gel (30 g), dichloromethane (75 mL), and 15% aqueous sulfuric acid (6 mL) was stirred at room temperature for 24 h. After neutralization with solid NaHCO$_3$ (2.1 g), filtration and washing of the silica gel (2×100 mL dichloromethane/methanol 25:1), the combined filtrates were concentrated. 3.10 g of crude ketone 4 was obtained.

$^1$H NMR (300 MHz, DMSO-$d_6$): δ2.55 (m, 2H), 2.69 (m, 2H), 2.84 (s, 6H), 3.06 (m, 2H), 6.06 (m, 1H), 7.03 (s, 1H), 8.18 (s, 1H).

Example 5
Preparation of Intermediate 5

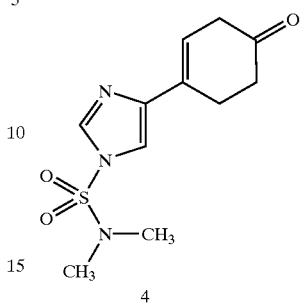

To a solution of the crude ketone 4 (3.1 g, approx. 10 mmol) in ethanol (50 mL) solid NaBH$_4$ (2.64 g, 69.8 mmol) was added. After stirring for 1 h at room temperature water (50 mL) was added, and the excess borohydride was destroyed by careful addition of 4N hydrochloric acid. The mixture was extracted (2×100 mL dichloromethane), the combined extracts were dried (MgSO$_4$) and concentrated and the residue was purified by column chromatography (silica gel, gradient elution with heptane/ethyl acetate). 0.91 g (34% for four steps) of the alcohol 5 was obtained as an oil.

$^1$H NMR (300 MHz, DMSO-$d_6$): δ1.55 (m, 1H), 1.80 (m, 1H), 2.00 (m, 1H), 2.32 (m, 3H), 2.77 (s, 6H), 3.78 (m, 1H), 4.70 (d, J=4 Hz, 1H), 5.86 (m, 1H), 6.89 (s, 1H), 8.03 (s,1H).

Example 6
Preparation of Compound 6 According to the Present Invention

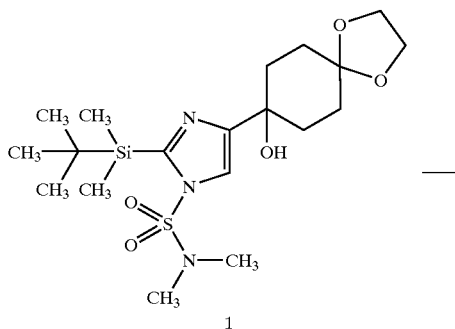

-continued

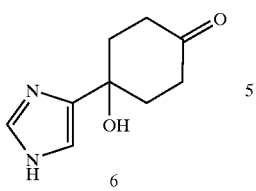

A mixture of the alcohol 1 (7.5 g, 16.8 mmol) and 10% aqueous sulfuric acid (100 mL) was refluxed for 1.5 h. When the mixture had cooled to room temperature it was washed with heptane, neutralized with solid $NaHCO_3$ (8.7 g) and concentrated under vacuum. The residue was extracted with hot ethanol and hot ethyl acetate. The extracts were concentrated and dried under reduced pressure. 3.89 g of crude ketone 6 was obtained.

$^1$H NMR (300 MHz, DMSO-$d_6$): δ2.05–2.22 (m, 6H), 2.60–2.75 (m, 2H), 6.99 (s, 1H), 7.68 (s, 1H).

Example 7

Preparation of Intermediate 7

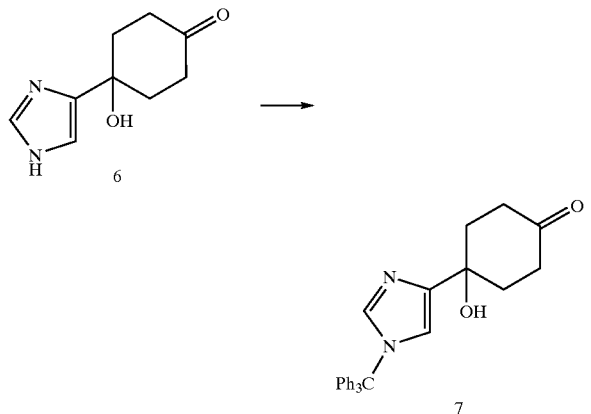

To a solution of the crude ketone 6 (3.89 g) in dichloromethane (200 mL) triethylamine (8.9 mL) and then trityl chloride (12.0 g, 43.2 mmol) were added. The resulting mixture was stirred at room temperature for 2 h, concentrated, and the residue was redissolved in ethyl acetate (30 mL). Filtration and concentration yielded a solid, which was recrystallized from ethyl acetate/heptane. 5.46 g (60%) of slightly triethylamine-contaminated ketone 7 was obtained.

HPLC (214 nm): Elution at 9.81 min. LCMS: MH$^+$ calcd.: 423, found: 423. $^1$H NMR (300 MHz, DMSO-$d_6$): δ1.90–2.25 (m, 6H), 2.53–2.69 (m, 2H), 5.18 (s, 1H), 6.81 (s, 1H), 7.10 (m, 6H), 7.30 (s, 1H), 7.40 (m, 9H).

Example 8

Preparation of Intermediates 8 and 9

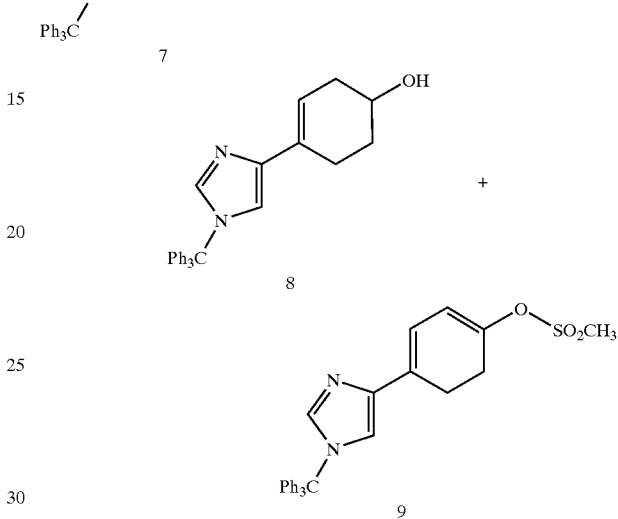

To a solution of ketone 7 (5.4 g, 12.8 mmol) in dichloromethane (50 mL) and triethylamine (10.6 mL, 76.5 mmol), a solution of methanesulfonyl chloride (3.0 mL, 38.6 mmol) in dichloromethane (10 mL) was dropwise added. The resulting mixture was stirred at room temperature for 3 h and then concentrated in a vacuum. The residue was redissolved in ethyl acetate (20 mL), filtered, concentrated and purified by column chromatography. 2.5 g of a mixture of two compounds was obtained. This mixture was redissolved in ethanol (30 mL) and treated at 0° C. with $NaBH_4$ (0.42 g, 11.1 mmol). After 1 h at 0° C. water (50 mL) was added, and the mixture was neutralized with 3N hydrochloric acid. The resulting mixture was concentrated to 50% of its volume, extracted (30 mL dichloromethane), the extracts were dried ($MgSO_4$), concentrated, and the residue was purified by column chromatography (silica gel, gradient elution with heptane/ethyl acetate). 0.69 g (17%) of alcohol 8 and 0.81 g (13%) of mesylate 9 was obtained.

Alcohol 8: HPLC (214 nm): Elution at 9.72 min. LCMS: MH$^+$ calcd.: 407, found: 407. $^1$H NMR (400 MHz, DMSO-$d_6$): δ1.45 (m, 1H), 1.78 (m, 1H), 1.96 (m, 1H), 2.05–2.40 (m, 3H), 3.71 (m, 1H), 4.57 (d, J=4 Hz, 1H), 6.18 (m, 1H), 6.74 (s, 1H), 7.10 (d, J=8 Hz, 6H), 7.30 (s, 1H), 7.34–7.45 (m, 9H). Anal. Calcd. for $C_{28}H_{26}N_2O$ (406.5): C, 82.73; H, 6.45; N, 6.89. Found: C, 82.38; H, 6.50; N, 6.77.

Mesylate 9: HPLC (214 nm): Elution at 11.65 min. LCMS: MH$^+$ calcd.: 483, found: 483. $^1$H NMR (400 MHz, DMSO-$d_6$): δ2.40–2.62 (m, 4H), 6.00 (d, J=7 Hz,1H), 6.42 (d, J=7 Hz, 1H), 6.99 (s, 1H), 7.12 (d, J=8 Hz, 6H), 7.35–7.45 (m, 10H).

Example 9
Preparation of Compound 10 According to the Present Invention

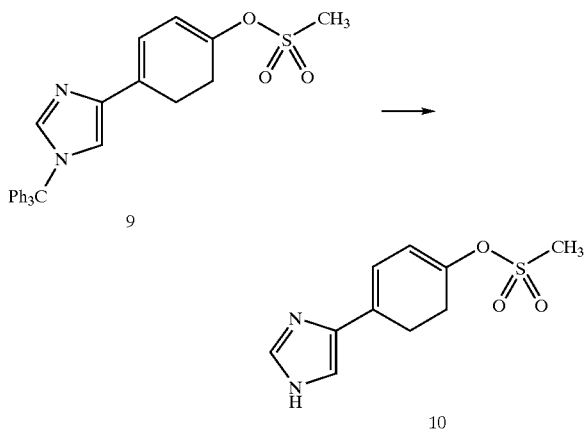

A mixture of mesylate 9 (0.28 g, 0.58 mmol), water (2 mL) and acetic acid (18 mL) was stirred at 60° C. for 1.5 h. After concentration and coevaporation with toluene the residue was purified by column chromatography (silica gel, gradient elution with heptane/ethyl acetate/methanol). 90 mg (64%) of mesylate 10 was obtained.

HPLC (214 nm): Elution at 6.17 min. LCMS: $MH^+$ calcd.: 243, found: 241 ($MH^+-H_2$). $^1H$ NMR (400 MHz, DMSO-$d_6$): δ2.50–2.75 (m, 4H), 3.32 (s, 3H), 6.00 (d, J=7 Hz, 1H), 6.20–6.45 (m, 1H), 7.04–7.30 (m, 1H), 7.65 (s, br, 1H), 11.90–12.30 (m, 1H).

Example 10
Preparation of Compound 11 According to the Present Invention

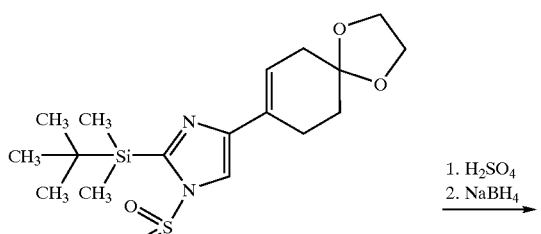

A mixture of the ketal 2 (5.0 g, 11.7 mmol) and 10% aqueous sulfuric acid (100 mL) was stirred at 100° C. for 3 h. The mixture was then neutralized by careful addition of solid $NaHCO_3$ (15.8 g), extracted with dichloromethane, the combined extracts were concentrated, and the residue was redissolved in ethanol (100 mL). To the resulting solution $NaBH_4$ (2.2 g, 58.5 mmol) was added, and the mixture was stirred at room temperature for 15 h. After addition of water (100 mL) and neutralization with 1N hydrochloric acid the mixture was concentrated to a volume of 25 mL. $K_2CO_3$ (13 g) was then added and the resulting mixture was extracted several times with ethyl acetate. The combined extracts were dried ($MgSO_4$) and concentrated. 1.74 g (91%) of alcohol 11 was obtained as a foam.

HPLC (214 nm): Elution at 2.58 min. LCMS: $MH^+$ calcd.: 165, found: 165. $^1H$ NMR (400 MHz, DMSO-$d_6$): δ1.52 (m, 1H), 1.83 (m, 1H), 2.01 (m, 1H), 2.20–2.48 (m, 3H), 3.73 (m, 1H), 6.05 (s, 1H), 6.92 (s, 1H), 7.55 (s, 1H).

Alternatively, compound 11 may also be prepared from intermediate 5 by acid catalyzed hydrolysis of the sulfur containing protective group.

Example 11
Preparation of Intermediate 8

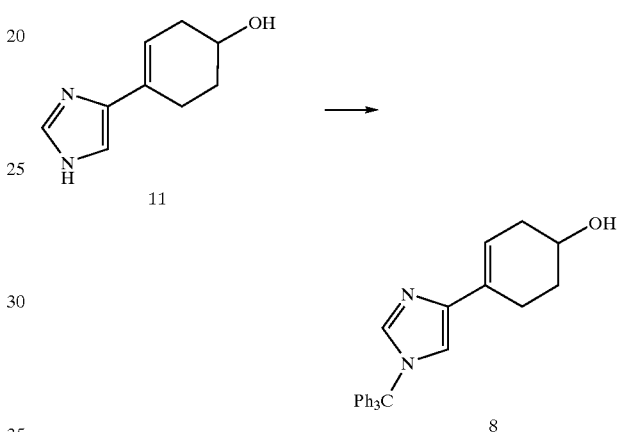

To a suspension of alcohol 11 (1.60 g, 9.80 mmol) in dichloromethane (100 mL) first triethylamine (4 mL) and then a solution of trityl chloride (3.03 g, 10.9 mmol) in dichloromethane (35 mL) were added. The resulting mixture was stirred at room temperature for 15 h and then chromatographed (silicagel, gradient elution with heptane/ethyl acetate). 2.0 g (50%) of the alcohol 8 was obtained, identical by $^1H$ NMR to the product obtained in Example 8.

Example 12
Preparation of Intermediates 12 and 13

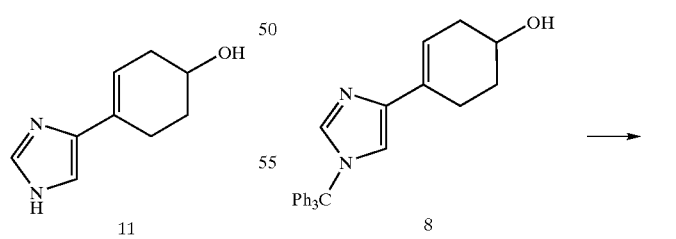

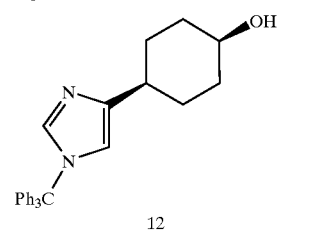

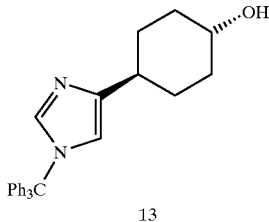

A mixture of olefin 8 (2.84 g, 6.99 mmol), ethanol (85 mL), glacial acetic acid (3.5 mL) and platinum oxide (0.41 g) was energically stirred at room temperature under a hydrogen atmosphere (27 atm) for 17 h. The mixture was then filtered, concentrated and the residue purified by column chromatography (silica gel, gradient elution with heptane/ethyl acetate/methanol 4:1:0 to 0:19:1). The products were obtained in three fractions: a) 1.40 g (49%) of pure isomer 13 (presumably trans); b) 0.32 g (11%) of a 1:1 mixture of 12 and 13; 0.40 g (14%) of pure isomer 12 (presumably cis).

12: m.p. (AcOEt) 215–217° C. $^1$H NMR (400 MHz, DMSO-$d_6$): δ1.12–1.30 (m, 4H), 1.80–1.90 (m, 4H), 2.32 (m, 1H), 3.35 (m, 1H), 4.45 (d, J=5Hz, 1H), 6.50 (s, 1H), 7.09 (d, J=8 Hz, 6H), 7.21 (s, 1H), 7.39 (m, 9H). Anal. calcd. for $C_{28}H_{28}N_2O$ (408.55): C, 82.31; H, 6.91; N, 6.86. Found: C, 82.19; H, 6.98; N, 6.85.

13: m.p. (AcOEt) 156–158° C. $^1$H NMR (400 MHz, DMSO-$d_6$): δ=1.40–1.76 (m, 8H), 2.45 (m, 1H), 3.73 (m, 1H), 4.24 (d, J=4 Hz, 1H), 6.51 (s, 1H), 7.08 (d, J=8 Hz, 6H), 7.23 (s, 1H), 7.39 (m, 9H). Anal. calcd. for $C_{28}H_{28}N_2O$ (408.55): C, 82.31; H, 6.91; N, 6.86. Found: C, 82.10; H, 6.94; N, 6.86.

Example 14

Preparation of Intermediate 14

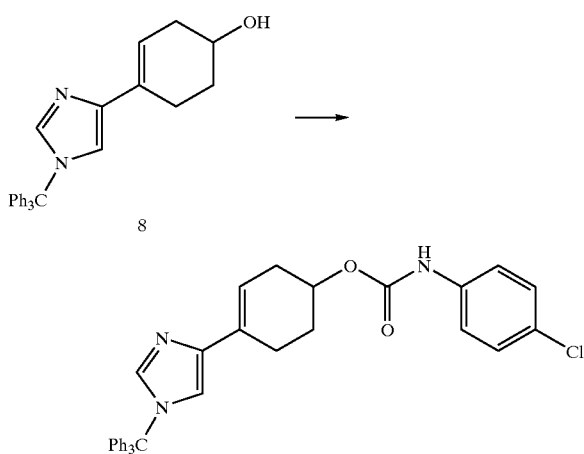

To a mixture of alcohol 8 (0.29 g, 0.74 mmol), toluene (5 mL) and triethylamine (0.3 mL) at 80° C. 4-chlorophenyl isocyanate (0.15 g, 0.96 mmol) was added. The resulting mixture was stirred at 80° C. for 2 h. The mixture was the allowed to cool down to room temperature and after filtration and concentration the residue was purified by column chromatography (silica gel, gradient elution with heptane/ethyl acetate). 0.29 g (70%) of carbamate 14 was obtained.

$^1$H NMR (400 MHz, DMSO-$d_6$): δ1.78–1.95 (m, 2H), 2.19–2.35 (m, 3H), 2.55 (m, 1H), 4.95 (m, 1H), 6.21 (m, 1H), 6.82 (s, 1H), 7.11 (m, 6H), 7.30 (d, J=8 Hz, 2H), 7.35 (s, 1H), 7.37–7.43 (m, 9H), 7.48 (d, J=8 Hz, 2H), 9.73 (s, exchangeable with $D_2O$, 1H).

Example 15

Preparation of Compound 15 According to the Present Invention

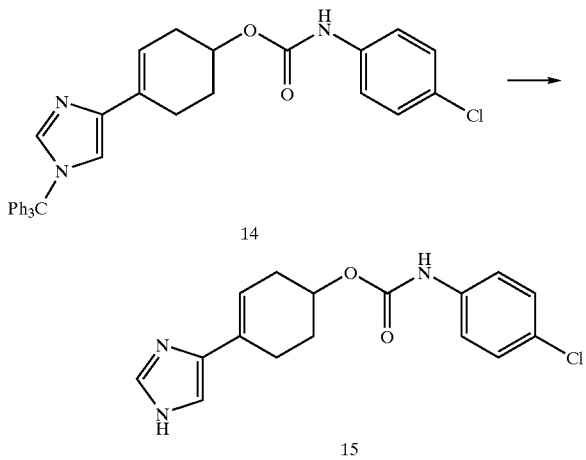

A mixture of carbamate 14 (0.29 g, 0.52 mmol), water (1.0 mL) and acetic acid (9 mL) was stirred at 60° C. for 1.5 h. The mixture was then neutralized by addition of saturated aqueous $NaHCO_3$-solution, and the product was extracted with ethyl acetate. The combined extracts were dried ($MgSO_4$), concentrated, and the residue was purified by column chromatography (silica gel, gradient elution with heptan/ethyl acetate/methanol), followed by recrystallization from heptane/ethyl acetate. 76 mg (46%) of carbamate 15 was obtained as colorless solid, m.p. 201–203° C.

HPLC (254 nm): Elution at 19.23 min, 99% pure. LCMS: $MH^+$ calcd.: 318, found: 318. $^1$H NMR (300 MHz, DMSO-$d_6$) (mixture of two tautomers or rotamers): δ1.79–2.05 (m, 2H), 2.20–2.64 (m, 4H), 4.95 (s, br, 1H), 5.98 (s, br, 0.35H), 6.20 (s, br, 0.65H), 6.90 (s, 0.35H), 7.08 (s, 0.65H), 7.31 (d, J=8 Hz, 2H), 7.49 (d, J=8 Hz, 2H), 7.57 (s, 0.65H), 7.59 (s, 0.35H), 9.76 (s, 1H), 11.90 (s, 0.65H), 12.13 (s, 0.35H). Anal. Calcd. for $C_{16}H_{16}ClN_3O_2$ (317.78): C, 60.48; H, 5.08; N, 13.22. Found: C, 60.27; H, 5.26; N, 12.67.

Example 16

Preparation of Compound 16 According to the Present Invention

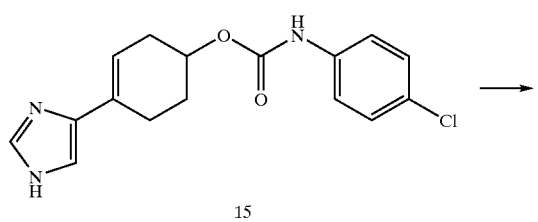

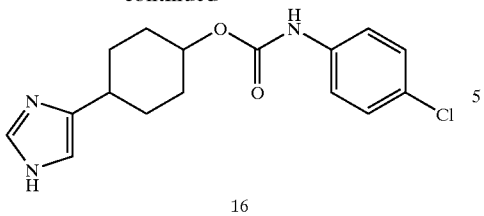

16

To a solution of carbamate 15 (70 mg, 0.22 mmol) in ethanol (9 mL) first acetic acid (1.0 mL) and then platinum oxide (23 mg) were added. The resulting mixture was stirred at room temperature under a hydrogen atmosphere (36 atm) for 4 d. The mixture was then filtered, concentrated and the residue was chromatographed (silica gel, gradient elution with ethyl acetate/methanol). 20 mg (28%) of carbamate 16 was obtained as a mixture of two diastereomers, m.p. 184–186° C.

HPLC (254 nm): Elution at 18.34 min (63%) and 20.54 min (26%). $^1$H NMR (400 MHz, DMSO-$d_6$) (mixture of two diastereomers): δ1.40–2.15 (m, 8H), 2.62 (m, 0.7H), 3.38 (m, 0.3H), 4.62 (m, 0.3H), 4.89 (m, 0.7H), 6.71 (s, br, 1H), 7.31 (m, 2H), 7.47 (m, 3H), 9.65 (s, 0.7H), 9.73 (s, 0.3H), 11.75 (s, br, 1H).

Example 17
Preparation of Intermediate 17

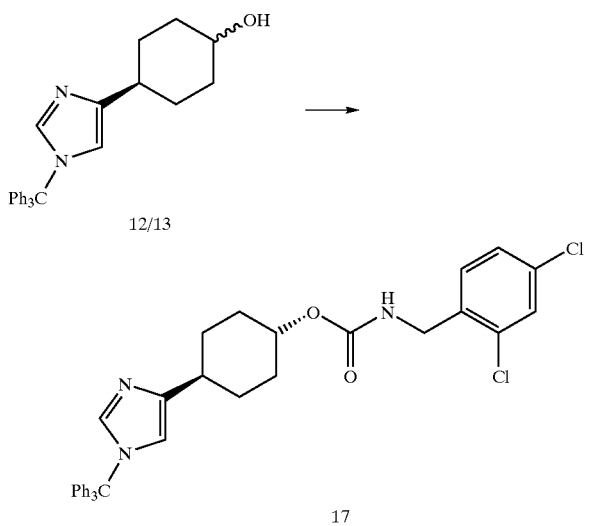

A mixture of alcohols 12/13 (1:1, 0.32 g, 0.78 mmol), toluene (5 mL), triethylamine (0.32 mL) and 3,5-dichlorobenzyl isocyanate (0.30 g, 1.50 mmol) was stirred at 80° C. for 2.5 h. Concentration and chromatographic purification gave 95 mg (20%) of diastereomerically pure carbamate 17 (presumably trans) as well as 190 mg (40%) of a mixture of two diastereomeric carbamates.

Single isomer 17: HPLC (214 nm): Elution at 14.22 min. LCMS: MH$^+$ calcd.: 610, found: 610. $^1$H NMR (300 MHz, DMSO-$d_6$): δ1.20–1.45 (m, 4H), 1.85–2.03 (m, 4H), 2.45 (m, 1H), 4.20 (s, 2H), 4.45 (s, br, 1H), 6.56 (s, 1H), 7.08 (m, 6H), 7.22 (s, 1H), 7.29–7.48 (m, 11H), 7.59 (m, 1H), 7.66 (t, J=6 Hz, 1H).

Example 18
Preparation of Compound 18 According to the Present Invention

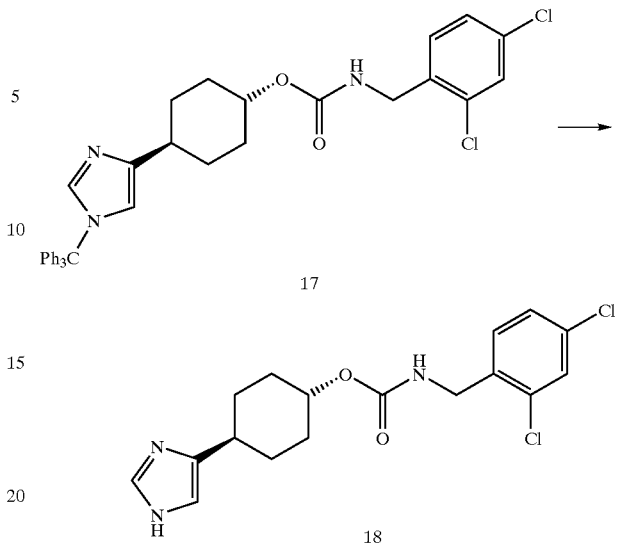

A mixture of carbamate 17 (95 mg, 0.16 mmol), water (1 mL) and acetic acid (9 mL) was stirred at 60° C. for 3 h. The mixture was then concentrated and the product was purified by column chromatography (silica gel, gradient elution with dichloromethane/ethyl acetate/methanol). 41 mg (72%) of carbamate 18 was obtained as a colourless powder, m.p. 149–151° C.

HPLC (254 nm): Elution at 20.65 min, 71% pure. LCMS: MH$^+$ calcd.: 368, found: 368. $^1$H NMR (400 MHz, DMSO-$d_6$): δ1.30–1.50 (m, 4H), 1.95–2.06 (m, 4H), 2.50 (m, 1H), 4.22 (s, br, 2H), 4.50 (s, br, 1H), 6.59 (s, br, 0.4H), 6.76 (s, br, 0.6H), 7.32 (d, J=8 Hz, 1H), 7.42 (dd, J=8, 1 Hz, 1H), 7.47 (s, 1H), 7.59 (d, J=1 Hz, 1H), 7.65 (m, 1H), 11.71 (s, br, 1H).

This reaction was repeated starting with a diastereomeric mixture of carbamate 17. The resulting mixture of detritylated compounds could not be separated by preparative column chromatography.

Example 19
Preparation of Compound 19 According to the Present Invention

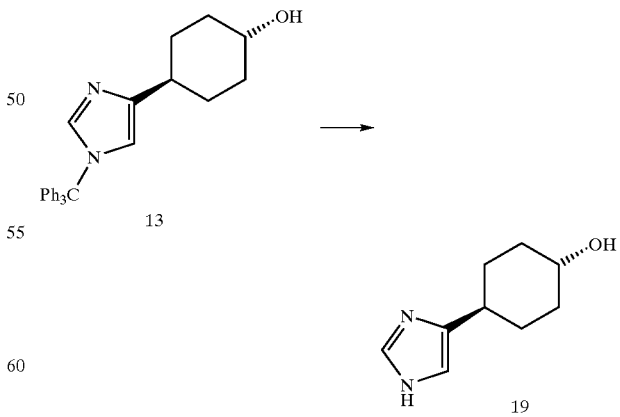

A mixture of alcohol 13 (100 mg, 0.24 mmol), water (2 mL) and acetic acid (18 mL) was stirred at 80° C. for 3 h. The mixture was then concentrated and the product was purified by column chromatography (silica gel, gradient elution with ethyl acetate/methanol). 28 mg (70%) of alcohol 19 was obtained as colourless solid, m.p. 196–198° C.

$^1$H NMR (400 MHz, DMSO-d$_6$): δ1.40–1.54 (m, 2H), 1.56–1.68 (m, 4H), 1.71–1.85 (m, 2H), 2.50 (m, 1H), 3.76 (s, br, 1H), 4.25 (s, br, 0.5H), 6.67 (s, 1H), 7.43 (s, 1H), 11.75 (s, br, 0.5H).

Example 20
Preparation of Intermediate 20

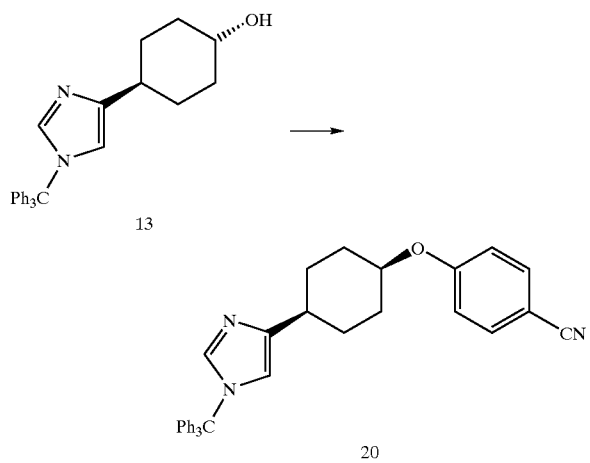

A solution of alcohol 13 (0.10 g, 0.24 mmol), triphenylphosphine (96 mg, 0.37 mmol) and 4-hydroxybenzonitrile (32 mg, 0.27 mmol) in pyridine (5 mL) was concentrated to dryness and the residue was then redissolved in dry THF (5 mL). To the resulting solution diethyl azodicarboxylate (64 mg, 0.37 mmol) was added and the mixture was then stirred at room temperature for 16 h. Then, more triphenylphosphine (96 mg) and diethyl azodicarboxylate (64 mg) were added and the mixture was heated to 50° C. for 3 h. Concentration and column chromatography gave 41 mg (33%) of ether 20.

Example 21
Preparation of Compound 21 According to the Present Invention

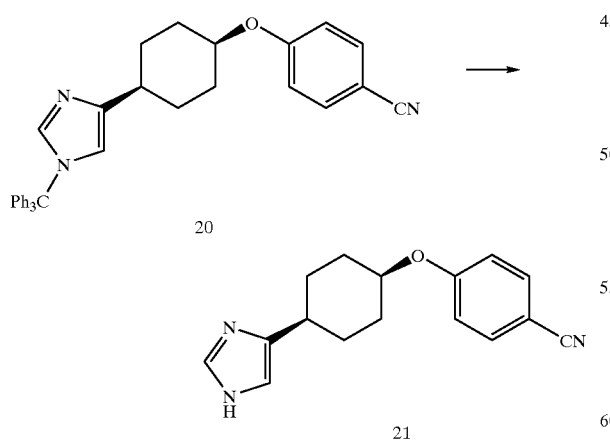

A mixture of ether 20 (40 mg, 0.078 mmol), water (1 mL) and acetic acid (9 mL) was stirred at 60° C. for 2 h. The mixture was then concentrated and the product was purified by recrystallization from ethyl acetate. 6.4 mg (31%) of ether 21 was obtained as a solid, m.p. 227–229° C.

HPLC (214 nm): Elution at 8.14 min. LCMS: MH$^+$ calcd.: 268, found: 268. $^1$H NMR (300 MHz, DMSO-d$_6$): δ1.40–1.65 (m, 4H), 1.98–2.20 (m, 4H), 2.60 (m, 1H), 4.49 (m, 1H), 6.61 (s, br, 0.4H), 6.79 (s, br, 0.6H), 7.11 (d, J=8 Hz, 2H), 7.50 (s, 1H), 7.72 (d, J=8 Hz, 2H).

Example 22
Preparation of Intermediate 22

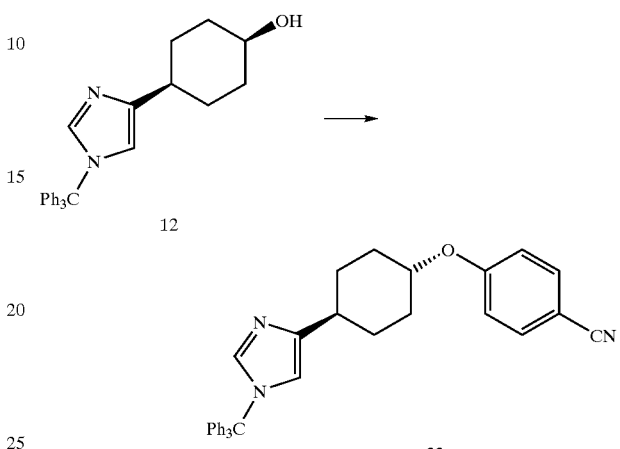

A solution of alcohol 12 (0.10 g, 0.24 mmol), triphenylphosphine (100 mg, 0.38 mmol) and 4-hydroxybenzonitrile (32 mg, 0.27 mmol) in pyridine (5 mL) was concentrated to dryness and the residue was then redissolved in dry THF (4 mL). To the resulting solution diethyl azodicarboxylate (64 mg, 0.37 mmol) was added and the mixture was then stirred at room temperature for 16 h. Concentration and column chromatography (silica gel, gradient elution with heptane/ethyl acetate) gave 90 mg (72%) of ether 22, m.p. 186–188° C., slightly contaminated with triphenylphosphine oxide.

HPLC (214 nm): Elution at 13.24 min. LCMS: MH$^+$ calcd.: 510, found: 510. $^1$H NMR (300 MHz, CDCl$_3$): δ1.65–1.95 (m, 6H), 2.00–2.10 (m, 2H), 2.69 (m, 1H), 4.62 (s, br, 1H), 6.55 (s, 1H), 6.95 (d, J=8 Hz, 2H), 7.14 (m, 6H), 7.30–7.41 (m, 12H).

Example 23
Preparation of Compound 23 According to the Present Invention

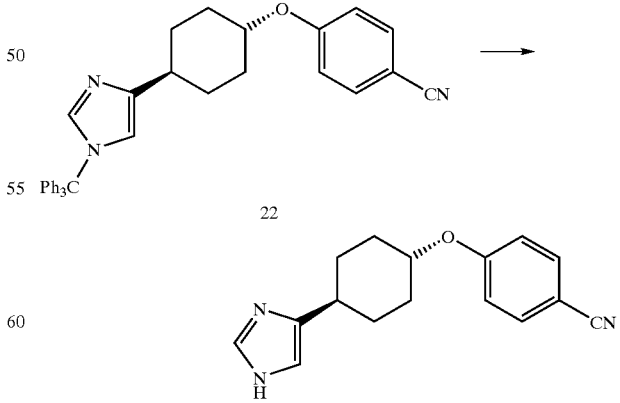

A mixture of ether 22 (90 mg, 0.18 mmol), water (2 mL) and acetic acid (18 mL) was stirred at 60° C. for 2 h. The mixture was then concentrated and the product was purified by column chromatography (silica gel, gradient elution with heptane/ethyl acetate). 20 mg (42%) of ether 23 was obtained.

HPLC (254 nm): Elution at 15.40 min, 100% pure. LCMS: MH+ calcd.: 268, found: 268. $^1$H NMR (400 MHz, CDCl$_3$): δ1.65–1.83 (m, 6H), 1.85–2.00 (m, 2H), 2.61–2.72 (m, 1H), 4.76 (s, br, 1H), 6.75 (s, 1H), 7.12 (d, J=8 Hz, 2H), 7.52 (s, 1H), 7.74 (d, J=8 Hz, 2H), 11.82 (s, br, 0.3H).

Example 24
Preparation of intermediate 24

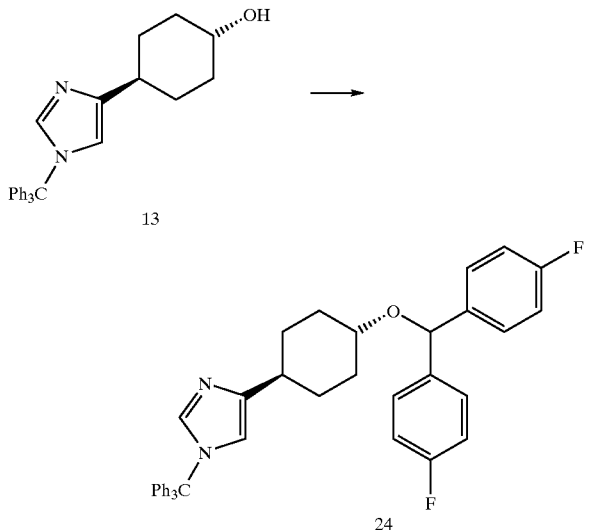

To a suspension of alcohol 13 (0.10 g, 0.24 mmol) in toluene (2.5 mL) sodium hydride (11 mg, 60% in mineral oil, 0.26 mmol) was added. 30 min later bis(4-fluorophenyl) methyl bromide (76 mg, 0.27 mmol) was added and the resulting mixture was heated to reflux for 20 h. Ethyl acetate (10 mL) and water (10 mL) were added, phases were separated, the organic phase was dried (MgSO$_4$), concentrated and the residue was purified by column chromatography (silica gel, gradient elution with heptane/ethyl acetate). 55 mg (38%) of ether 24 was obtained.

HPLC (214 nm): Elution at 15.24 min. LCMS: MH+ calcd.: 611, found: 611. $^1$H NMR (300 MHz, CDCl$_3$): δ1.45–1.60 (m, 2H), 1.75–1.95 (m, 6H), 2.62 (m, 1H), 3.58 (m, 1H), 5.41 (s, 1H), 6.52 (s, 1H), 6.90–7.45 (m, 24H).

Example 25
Preparation of Compound 25 According to the Present Invention

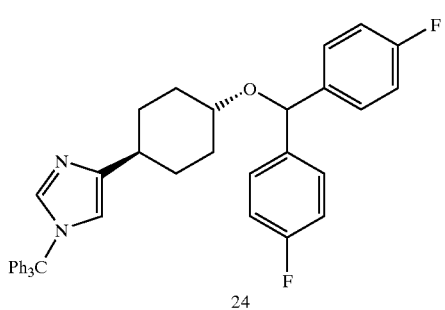

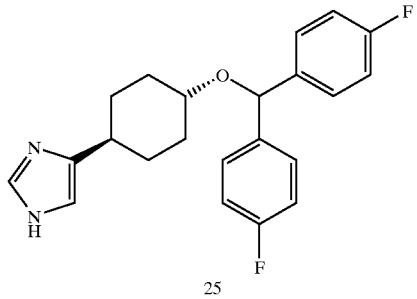

A mixture of ether 24 (55 mg, 0.09 mmol), water (2 mL) and acetic acid (18 mL) was stirred at 60° C. for 2 h. The mixture was then concentrated and the product was purified by column chromatography (silica gel, gradient elution with methanol/ethyl acetate). 10 mg (30%) of ether 25 was obtained.

HPLC (214 nm): Elution at 10.97 min. LCMS: MH+ calcd.: 369, found: 369. $^1$H NMR (400 MHz, CDCl$_3$): δ1.49–1.60 (m, 2H), 1.78–1.99 (m, 6H), 2.68 (m, 1H), 3.62 (s, br, 1H), 5.41 (s, 1H), 6.79 (s, 1H), 6.98 (m, 4H), 7.28 (m, 4H), 7.60 (s, 1H).

Example 26
Preparation of Intermediates 26 and 27

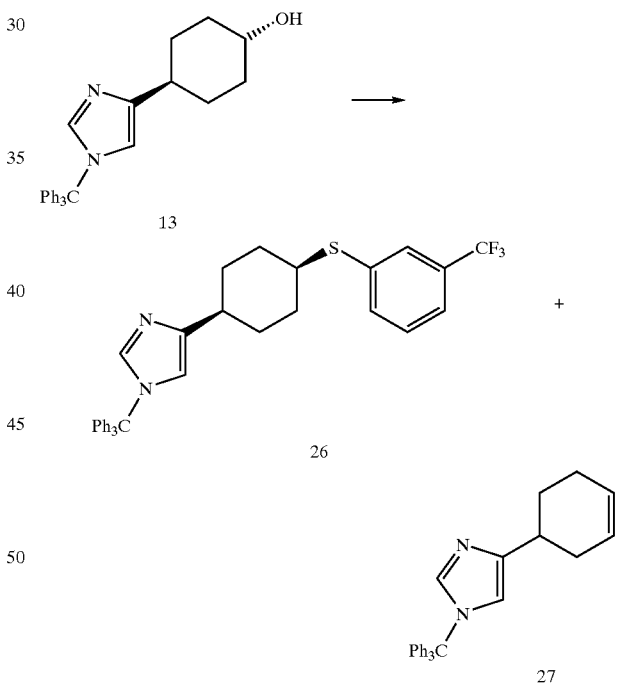

To a mixture of alcohol 13 (0.20 g, 0.49 mmol), 3-(trifluoromethyl)thiophenol (0.09 g, 0.51 mmol), triphenylphosphine (0.20 g, 0.76 mmol) and THF (10 mL) a solution of diethyl azodicarboxylate (0.13 g, 0.76 mmol) in THF (1.0 mL) was added. After stirring for 2 h at room temperature more 3-(trifluoromethyl)thiophenol (0.09 g), triphenylphosphine (0.20 g) and diethyl azodicarboxylate (0.13 g) were added and stirring at room temperature was continued for 5 days. The mixture was concentrated and the products were purified by column chromatography (silica gel, gradient elution with heptane/ethyl acetate). 67 mg (35%) of cyclohexene 27 and a mixture of thioether 26 and cyclohexene 27 (50 mg) was obtained.

Thioether 26:HPLC (214 nm): Elution at 15.04 min. LCMS: MH⁺ calcd.: 569, found: 569. ¹H NMR (300 MHz, CDCl₃): δ1.39–1.60 (m, 2H), 2.00–2.19 (m, 6H), 2.56 (m, 1H), 3.15 (m, 1H), 6.48 (s, 1H), 7.05–7.62 (m, 19H).

Olefin 27:HPLC (214 nm): Elution at 12.56 min. LCMS: MH⁺ calcd.: 391, found: 391. ¹H NMR (300 MHz, CDCl₃): δ1.58–1.70 (m, 1H), 1.99–2.20 (m, 4H), 2.28–2.43 (m, 1H), 2.78–2.90 (m, 1H), 5.69 (m, 2H), 6.53 (s, 1H), 7.13 (m, 6H), 7.28–7.45 (m, 10 H).

Example 28

Preparation of Compound 28 According to the Present Invention

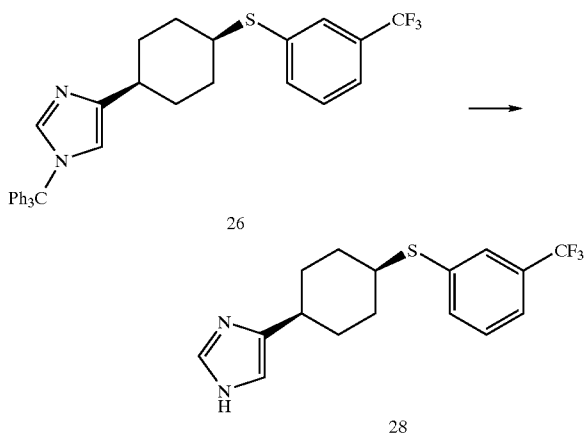

A mixture of thioether 26 (50 mg, approx. 0.09 mmol, contaminated with olefin 27), water (1 mL) and acetic acid (10 mL) was heated to 65° C. for 1.5 h. The mixture was then concentrated and to the residue water, ethyl acetate and triethylamine (0.1 mL) were added. The organic phase was separated, dried (MgSO₄) and concentrated. Column chromatography (silica gel, gradient elution with ethyl acetate/methanol) yielded 14 mg (49%) of the thioether 28 (contaminated with the olefin 31).

HPLC (214 nm): Elution at 10.04 min. LCMS: MH⁺ calcd.: 327, found: 327. ¹H NMR (300 MHz, CDCl₃): δ1.39–1.60 (m, 4H), 2.05–2.25 (m, 4H), 2.65 (m, 1H), 3.15 (m, 1H), 6.74 (s, 1H), 7.34–7.50 (m, 2H), 7.57 (m, 2H), 7.61 (s, 1H).

Example 29

Preparation of Intermediates 29 and 27

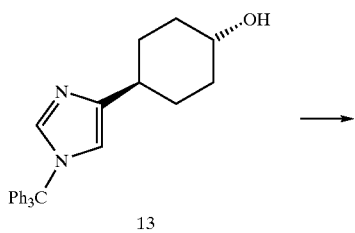

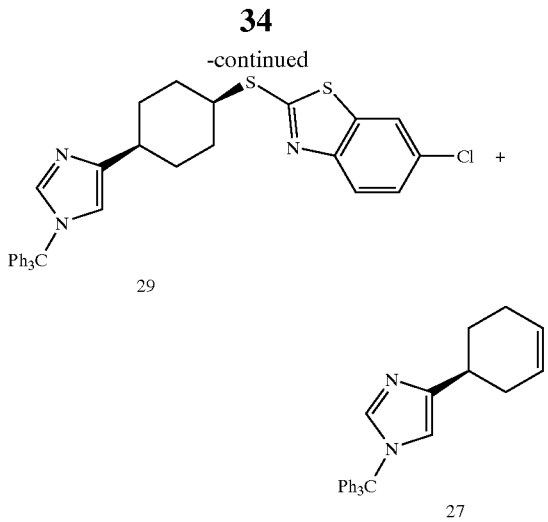

To a mixture of alcohol 13 (0.20 g, 0.49 mmol), 5-chloro-2-mercaptobenzothiazole (0.10 g, 0.50 mmol), triphenylphosphine (0.20 g, 0.76 mmol) and THF (10 mL) a solution of diethyl azodicarboxylate (0.13 g, 0.76 mmol) in THF (1.0 mL) was added. After stirring for 2 h at room temperature more 5-chloro-2-mercaptobenzothiazole (0.05 g, 0.25 mmol), triphenylphosphine (0.20 g) and diethyl azodicarboxylate (0.13 g) were added and stirring at room temperature was continued for 20 h. The mixture was concentrated and the products were purified by column chromatography (silica gel, gradient elution with heptane/ethyl acetate). 34 mg (11%) of thioether 29 and 134 mg (70%) of olefin 27 were obtained.

Thioether 29:HPLC (214 nm): Elution at 15.38 min. LCMS: MH⁺ calcd.: 593, found: 592. ¹H NMR (300 MHz, CDCl₃): δ1.59 (m, 4H), 2.16 (m, 2H), 2.34 (m, 2H), 2.61 (m, 1H), 3.84 (m, 1H), 6.52 (s, 1H), 7.13 (m, 6H), 7.25 (dd, J=8, 1 Hz, 1H), 7.31 (m, 10H), 7.62 (d, J=8 Hz, 1H), 7.82 (d, J=1 Hz, 1H).

Example 30

Preparation of Compound 30 According to the Present Invention

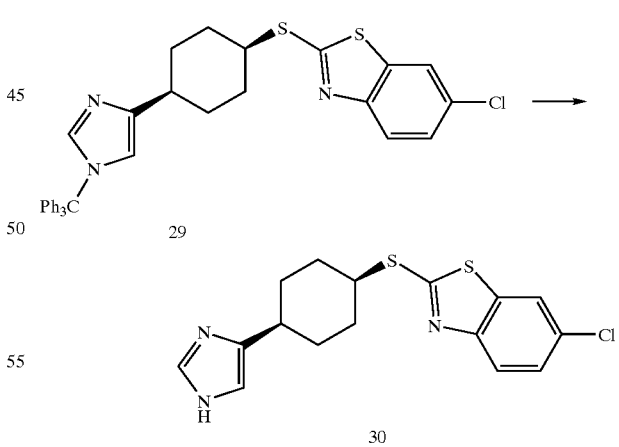

A mixture of thioether 29 (34 mg, 0.06 mmol), water (1 mL) and acetic acid (10 mL) was heated to 65° C. for 1.5 h. The mixture was then concentrated and to the residue water, ethyl acetate and triethylamine (0.1 mL) were added. The organic phase was separated, dried (MgSO₄) and concentrated. Column chromatography (silica gel, gradient elution with ethyl acetate/methanol) yielded 16 mg (80%) of the thioether 30.

HPLC (214 nm): Elution at 10.17 min. LCMS: MH+ calcd.: 350, found: 350. ¹H NMR (400 MHz, DMSO-d₆): δ1.59 (m, 4H), 2.07 (m, 2H), 2.28 (m, 2H), 2.58 (m, 1H), 3.84 (m, 1H), 6.73 (s, 1H), 7.44 (dd, J=8, 1 Hz, 1H), 7.51 (s, 1H), 7.97 (d, J=1H), 8.06 (d, J=8 Hz, 1H), 11.80 (s, br, 0.5H).

Example 31

Preparation of Compound 31 According to the Present Invention

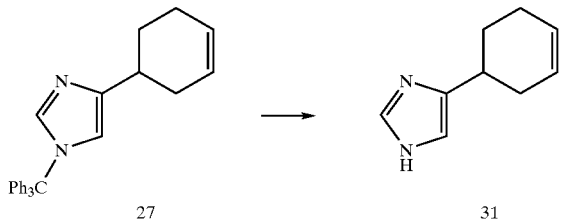

A mixture of thioether 27 (0.20 g, 0.51 mmol), water (2 mL) and acetic acid (18 mL) was heated to 65° C. for 2 h. The mixture was then concentrated and to the residue water, ethyl acetate and triethylamine (0.1 mL) were added. The organic phase was separated, dried (MgSO₄) and concentrated. Column chromatography (silica gel, gradient elution with ethyl acetate/methanol) yielded 50 mg (66%) of olefin 31 as an oil.

HPLC (214 nm): Elution at 6.22 min. LCMS: MH+ calcd.: 149, found: 149. ¹H NMR (300 MHz, CDCl₃): δ1.69 (m, 1H), 2.00–2.25 (m, 4H), 2.40 (m, 1H), 2.94 (m, 1H), 5.74 (m, 2H), 5.79 (s, 1H), 7.50 (s, br, 1H), 7.62 (s, 1H).

Pharmacological Methods

Histamine H3 Receptor Binding Assay

The ability of the compounds to interact with the histamine H3 receptor was determined by an in vitro binding assay. Rat cerebral cortex was homogenized in ice cold K-Hepes, 5 mM MgCl₂ pH 7.1 buffer. After two differential centrifugations the last pellet was resuspended in fresh Hepes buffer containing 1 mg/mL Bacitracin. Aliquots of the membrane suspension (400 mg/mL) were incubated for 60 min at 25° C. with 30 pM [¹²⁵I]-iodoproxifan, a known histamine H3 receptor antagonist, and the test compound at various concentrations. The incubation was stopped by dilution with ice-cold medium, followed by rapid filtration through Whatman GF/B filters pretreated for 1 h with 0.5% polyethyleneimine. The radioactivity retained on the filters was counted using a Cobra II auto gamma counter. The radioactivity of the filters was indirectly proportional to the binding affinity of the tested compound. The results were analyzed by nonlinear regression analysis.

When tested, the present compounds of formula I showed a high binding affinity to the histamine H3 receptor.

Preferably, the compounds according to the invention have an IC₅₀ value as determined by the assay of less than 1 μM, more preferred of less than 500 nM and even more preferred of less than 100 nM.

Furthermore, in a similar way binding assays were carried out in order to determine the ability of the present compounds to interact with the histamine H1 receptor (reference compound [¹²⁵I]-pyrilamine) and the histamine H2 receptor (reference compound [¹²⁵I]-aminopotentidine), respectively. These assays showed that the present compounds do not show a high affinity for these receptors and hence are very specific to the histamine H3 receptor.

The Open Cage Schedule-fed Rat Model

The ability of the present compounds to reduce weight was determined using the in vivo open cage Schedule-fed rat model.

Sprague-Dawley (SD) male rats of an age of about 1½ to 2 months and a weight of about 250 g were habituated to the presence of food (Altromin pelleted rat chow) in their home cage only during three hours in the morning from 9 to 12 a.m. all days a week. Water was present ad libitum. As the consumption of food stabilized after 7 to 9 days, the animals were ready for use.

The animals were tested twice a week. During the test sessions, the test compound was administered intraperitoneally 30 minutes before the start of the sessions. One group of 9 animals was administered the test compound at a dose of 15 mg/kg and another group of 11 animals was administered the test compound at a dose of 30 mg/kg. A control group of 11 animals was administered the vehicle consisting of NaCl 0.9% and Chremophor 5%. Food and water intake were monitored at 1, 2 and 3 h post administration.

During the test period the animals were weighed weekly and if necessary extra food was given in order to ensure that the weight gain was 3 to 5 g per week corresponding to the normal weight gain for SD male rats at this age.

Any side effects could rapidly be discovered (barrel-rolling, bushy fur etc.) since the animals were kept in transparent plastic cages to enable continuous monitoring.

When tested the compounds significantly and dose-dependently inhibit food intake.

What is claimed is:

1. A compound of formula I

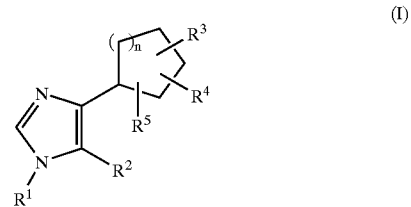

(I)

wherein the carbocyclic ring does or does not contain one or two double bonds;

n represents 1 or 2;

$R^1$ is hydrogen or a functional group which can be converted to hydrogen in vivo;

$R^2$ is hydrogen, $C_{1-6}$-alkyl, cyano or halogen;

$R^3$ is hydrogen, hydroxy or halogen;

$R^4$ is hydrogen, hydroxy or cyano;

$R^5$ is hydrogen;

aryl unsubstituted or substituted with halogen, $C_{1-6}$alkoxy, $C_{1-6}$-alkyl, trifluoromethyl, $C_{3-8}$-cycloalkyl, aryl or heteroaryl;

$C_{1-6}$-alkyl unsubstituted or substituted with $C_{3-8}$-cycloalkyl unsubstituted or substituted with halogen, $C_{1-6}$-alkoxy, $C_{1-6}$-alkyl, trifluoromethyl, $C_{3-8}$-cycloalkyl, aryl or heteroaryl;

aryl unsubstituted or substituted with halogen, $C_{1-6}$-alkoxy, $C_{1-6}$-alkyl, trifluoromethyl, $C_{3-8}$-cycloalkyl, aryl or heteroaryl; or heteroaryl unsubstituted or substituted with halogen, $C_{1-6}$-alkoxy, $C_{1-6}$-alkyl, trifluoromethyl, $C_{3-8}$-cycloalkyl, aryl or heteroaryl;

—X—$R^6$ wherein X is —O— or —S—; and $R^6$ is hydrogen;

$C_{1-6}$-alkyl unsubstituted or substituted with halogen, $C_{1-6}$-alkoxy, trifluoromethyl, $C_{3-8}$-cycloalkyl, aryl or heteroaryl where the $C_{3-8}$-cycloalkyl, aryl and heteroaryl groups are unsubstituted or substituted with halogen, $C_{1-6}$-alkoxy, $C_{1-6}$-alkyl, trifluoromethyl, cyano, $C_{3-8}$-cycloalkyl, aryl or heteroaryl;

$C_{3-8}$-cycloalkyl unsubstituted or substituted with halogen, $C_{1-6}$-alkoxy, $C_{1-6}$-alkyl, trifluoromethyl, $C_{3-8}$-cycloalkyl, aryl or heteroaryl;

aryl unsubstituted or substituted with halogen, $C_{1-6}$-alkoxy, $C_{1-6}$-alkyl, trifluoromethyl, cyano, $C_{3-8}$-cycloalkyl, aryl or heteroaryl;

heteroaryl unsubstituted or substituted with halogen, $C_{1-6}$-alkoxy, $C_{1-6}$-alkyl, trifluoromethyl, $C_{3-8}$-cycloalkyl, aryl or heteroaryl;

—$CONR^7R^8$ wherein $R^7$ and $R^8$ independently are
hydrogen;

$C_{1-6}$-alkyl unsubstituted or substituted with halogen, $C_{1-6}$-alkoxy, trifluoromethyl, $C_{3-8}$-cycloalkyl, aryl or heteroaryl where the $C_{3-8}$-cycloalkyl, aryl and heteroaryl groups are unsubstituted or substituted with halogen, $C_{1-6}$-alkoxy, $C_{1-6}$-alkyl, trifluoromethyl, cyano, $C_{3-8}$-cycloalkyl, aryl or heteroaryl;

$C_{3-8}$-cycloalkyl unsubstituted or substituted with halogen, $C_{1-6}$-alkoxy, $C_{1-6}$-alkyl, trifluoromethyl, $C_{3-8}$-cycloalkyl, aryl or heteroaryl;

aryl unsubstituted or substituted with halogen, $C_{1-6}$-alkoxy, $C_{1-6}$-alkyl, trifluoromethyl, cyano, $C_{3-8}$-cycloalkyl, aryl or heteroaryl; or heteroaryl unsubstituted or substituted with halogen, $C_{1-6}$-alkoxy, $C_{1-6}$-alkyl, trifluoromethyl, $C_{3-8}$-cycloalkyl, aryl or heteroaryl; or $R^7$ and $R^8$ together form a 3 to 8 membered, saturated or unsaturated carbocyclic or heterocyclic ring which is unsubstituted or substituted with halogen, $C_{1-6}$-alkoxy, $C_{1-6}$-alkyl, trifluoromethyl, $C_{3-8}$-cycloalkyl, aryl or heteroaryl; or

—$SO_2R^7$;

provided that when X is —S—, $R^6$ must not be hydrogen, —$CONR^7R^8$ or —$SO_2R^7$; or —$CONR^7R^8$; or $R^4$ and $R^5$ taken together represent =O;

provided that when $R^2$ is hydrogen, then $R^3$, $R^4$ or $R^5$ must not be methyl or ethyl in the 1 position;

when n is 2, $R^1$ is —$CPh_3$, $R^2$ and $R^3$ are hydrogen and $R^4$ is cyano in the 1 position, then $R^5$ must not be hydrogen;

when n is 2 and $R^1$, $R^2$, $R^3$ and $R^4$ are hydrogen, then $R^5$ must not be hydrogen; and when n is 1 or 2, and $R^1$, $R^2$, $R^3$ and $R^4$ are hydrogen, then $R^5$ must not be hydroxy;

or any optical or geometric isomer or tautomeric form thereof or a pharmaceutically acceptable salt thereof.

2. A compound according to claim 1 wherein
$R^5$ is
aryl unsubstituted or substituted with halogen, $C_{1-6}$-alkoxy, $C_{1-6}$-alkyl, trifluoromethyl, $C_{3-8}$-cycloalkyl, aryl or heteroaryl;

$C_{1-6}$-alkyl unsubstituted or substituted with
$C_{3-8}$-cycloalkyl unsubstituted or substituted with halogen, $C_{1-6}$-alkoxy, $C_{1-6}$-alkyl, trifluoromethyl, $C_{3-8}$-cycloalkyl, aryl or heteroaryl;

aryl unsubstituted or substituted with halogen, $C_{1-6}$-alkoxy, $C_{1-6}$-alkyl, trifluoromethyl, $C_{3-8}$-cycloalkyl, aryl or heteroaryl; or heteroaryl unsubstituted or substituted with halogen, $C_{1-6}$-alkoxy, $C_{1-6}$-alkyl, trifluoromethyl, $C_{3-8}$-cycloalkyl, aryl or heteroaryl;

—X—$R^6$ wherein X is —O— or —S—; and
$R^6$ is
hydrogen;

$C_{1-6}$-alkyl unsubstituted or substituted with halogen, $C_{1-6}$-alkoxy, trifluoromethyl, $C_{3-8}$-cycloalkyl, aryl or heteroaryl where the $C_{3-8}$-cycloalkyl, aryl and heteroaryl groups are unsubstituted or substituted with halogen, $C_{1-6}$-alkoxy, $C_{1-6}$-alkyl, trifluoromethyl, cyano, $C_{3-8}$-cycloalkyl, aryl or heteroaryl;

$C_{3-8}$-cycloalkyl unsubstituted or substituted with halogen, $C_{1-6}$-alkoxy, $C_{1-6}$-alkyl, trifluoromethyl, $C_{3-8}$-cycloalkyl, aryl or heteroaryl;

aryl unsubstituted or substituted with halogen, $C_{1-6}$-alkoxy, $C_{1-6}$-alkyl, trifluoromethyl, cyano, $C_{3-8}$-cycloalkyl, aryl or heteroaryl;

heteroaryl unsubstituted or substituted with halogen, $C_{1-6}$-alkoxy, $C_{1-6}$-alkyl, trifluoromethyl, $C_{3-8}$-cycloalkyl, aryl or heteroaryl;

—$CONR^7R^8$ wherein $R^7$ and $R^8$ independently are
hydrogen;

$C_{1-6}$-alkyl unsubstituted or substituted with halogen, $C_{1-6}$-alkoxy, trifluoromethyl, $C_{3-8}$-cycloalkyl, aryl or heteroaryl where the $C_{3-8}$-cycloalkyl, aryl and heteroaryl groups are unsubstituted or substituted with halogen, $C_{1-6}$-alkoxy, $C_{1-6}$-alkyl, trifluoromethyl, cyano, $C_{3-8}$-cycloalkyl, aryl or heteroaryl;

$C_{3-8}$-cycloalkyl unsubstituted or substituted with halogen, $C_{1-6}$-alkoxy, $C_{1-6}$-alkyl, trifluoromethyl, $C_{3-8}$-cycloalkyl, aryl or heteroaryl;

aryl unsubstituted or substituted with halogen, $C_{1-6}$-alkoxy, $C_{1-6}$-alkyl, trifluoromethyl, cyano, $C_{3-8}$-cycloalkyl, aryl or heteroary; or heteroaryl unsubstituted or substituted with halogen, $C_{1-6}$-alkoxy, $C_{1-6}$-alkyl, trifluoromethyl, $C_{3-8}$-cycloalkyl, aryl or heteroaryl; or $R^7$ and $R^8$ together form a 3 to 8 membered, saturated or unsaturated carbocyclic or heterocyclic ring which is unsubstituted or substituted with halogen, $C_{1-6}$-alkoxy, $C_{1-6}$-alkyl, trifluoromethyl, $C_{3-8}$-cycloalkyl, aryl or heteroaryl; or

—$SO_2R^7$;

with the proviso that when X is —S—, $R^6$ must not be hydrogen, —$CONR^7R^8$ or —$SO_2R^7$; or —$CONR^7R^8$; or $R^4$ and $R^5$ taken together represent =O.

3. A compound according to claim 1 wherein n is 2.

4. A compound according to claim 3 wherein the carbocyclic ring is cyclohexyl.

5. A compound according to claim 1 wherein $R^1$ and $R^2$ are both hydrogen.

6. A compound according to claim 1 wherein $R^3$ and $R^4$ are both hydrogen.

7. A compound according to claim 1 wherein $R^5$ is in the 4-position.

8. A compound according to claim 1 wherein $R^5$ is —X—$R^6$.

9. A compound according to claim 8 wherein $R^6$ is
hydrogen;
$C_{1-6}$-alkyl unsubstituted or substituted with halogen, $C_{1-6}$-alkoxy, trifluoromethyl, $C_{3-8}$-cycloalkyl, aryl or heteroaryl where the $C_{3-8}$-cycloalkyl, aryl and heteroaryl groups are unsubstituted or substituted with halogen, $C_{1-6}$alkoxy, $C_{1-6}$alkyl, trifluoromethyl, cyano, $C_{3-8}$-cycloalkyl, aryl or heteroaryl;
aryl unsubstituted or substituted with halogen, $C_{1-6}$-alkoxy, $C_{1-6}$-alkyl, trifluoromethyl, cyano, $C_{3-8}$-cycloalkyl, aryl or heteroaryl; or
—$CONR^7R^8$.

10. A compound according to claim 9 wherein X is —O— and $R^6$ is
$C_{1-6}$-alkyl substituted with phenyl which is unsubstituted or substituted with halogen, cyano or trifluoromethyl;
phenyl unsubstituted or substituted with halogen, cyano or trifluoromethyl; or
—$CONR^7R^8$ wherein $R^7$ and $R^8$ independently are
hydrogen;
$C_{1-6}$-alkyl substituted with phenyl which is substituted with halogen, cyano or trifluoromethyl; or
phenyl unsubstituted or substituted with halogen, cyano or trifluoromethyl.

11. A pharmaceutical composition comprising a therapeutically effective amount of at least one compound of claim 1 together with one or more pharmaceutically acceptable carriers or diluents.

12. The pharmaceutical composition of claim 11 in unit dosage form, comprising from about 0.05 mg to about 1000 mg of the compound.

13. The pharmaceutical composition of claim 12 in unit dosage form, comprising from about 0.1 mg to about 500 mg of the compound.

14. The pharmaceutical composition of claim 13 in unit dosage form, comprising from about 0.5 mg to about 200 mg of the compound.

15. A method for treating disorders and diseases associated with overweight or obesity comprising administering to a subject in need thereof an effective amount of a compound of claim 1.

16. A method of treating eating disorders comprising administering to a subject in need thereof an effective amount of a compound of claim 1.

17. A method of treating disorders mediated by the serotonin-3 receptor (5-HT3) comprising administering to a subject in need thereof an effective amount of a compound of claim 1.

18. The method of claim 17, wherein the disorder is emesis.

19. A method of treating disorders mediated by the vanilloid receptor comprising administering to a subject in need thereof an effective amount of a compound of claim 1.

20. The method of claim 19, wherein the disorder is pain, neurogenic inflammation or obesity.

21. A method of treating disorders mediated by the alpha-2 adrenergic receptor comprising administering to a subject in need thereof an effective amount of a compound of claim 1.

22. A method for the treatment of disorders mediated by the histamine H3 receptor, the method comprising administering to a subject in need thereof an effective amount of a compound of claim 1.

23. The method according to claim 22 wherein the effective amount of the compound is in the range of from about 0.05 mg to about 1000 mg.

24. The method of claim 23, wherein the effective amount of the compound is in the range of from about 0.1 mg to about 500 mg.

25. The method of claim 24, wherein the effective amount of the compound is in the range of from about 0.5 mg to about 200 mg per day.

26. A process for the preparation of a compound of formula Id

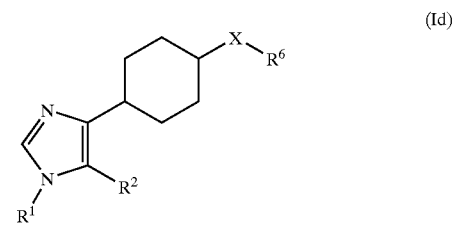

(Id)

according to claim 1 and optical or geometric isomer or tautomeric forms thereof, or a pharmaceutically acceptable salt thereof, comprising the steps of
a) treating a 4-(4-oxocyclohex-1-enyl)imidazole compound comprising formula V

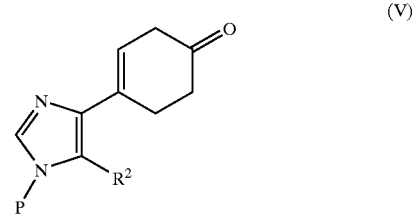

(V)

wherein P is a protecting group, with a reducing agent to give a 4-(4-hydroxycyclohex-1-enyl)imidazole compound of formula Ib'

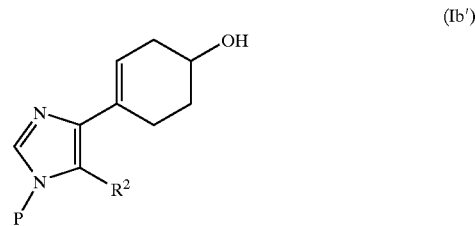

(Ib')

b) treating the compound of formula Ib' with a hydrogenating agent and a catalyst to give a 4-(4-hydroxycyclohexyl)imidazole compound of formula Ia'

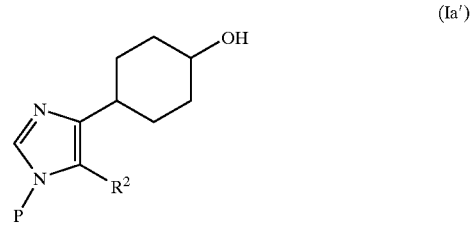

(Ia')

and
c)
i) when X is oxygen and $R^6$ is hydrogen:
removing P from the compound of formula Ia' to give a compound of formula Id wherein $R^1$ is hydrogen and, optionally replacing the hydrogen at $R^1$ in the compound of formula Id with a functional group which can be converted to hydrogen in vivo, or ii) when X is oxygen and $R^6$ is $C_{1-6}$-alkyl, $C_{3-8}$-cycloalkyl, aryl or heteroaryl:
treating the compound of formula Ia' with $R^6$-Hal wherein Hal represents halogen and removing P to give a compound of formula Id wherein $R^1$ is hydrogen and, optionally replacing the hydrogen at R1 in the compound of formula Id with a functional group which can be converted to hydrogen in vivo, or iii) when X is oxygen and $R^6$ is —$CONR^7R^8$:
reacting the compound of formula Ia' with Cl—CO—$NR^7R^8$ or O=C=N—$R^7$ and removing P to give a compound of formula Id wherein $R^1$ is hydrogen and, optionally replacing the hydrogen at $R^1$ in the compound of formula Id with a functional group which can be converted to hydrogen in vivo, or iv) when X is oxygen and $R^6$ is —$SO_2R^7$:
reacting the compound of formula Ia' with Cl—$SO_2$—$R^7$ and removing P to give a compound of formula Id wherein $R^1$ is hydrogen and, optionally replacing the hydrogen at $R^1$ in the compound of formula Id with a functional group which can be converted to hydrogen in vivo, or v) when X is sulfur and $R^6$ is $C_{1-6}$-alkyl, $C_{3-8}$-cycloalkyl, aryl or heteroaryl: replacing the hydroxy group with $R^6$—SH and removing P to give a compound of formula Id wherein $R^1$ is hydrogen and, optionally replacing the hydrogen at $R^1$ in the compound of formula Id with a functional group which can be converted to hydrogen in vivo; and (d) optionally separating the compound of formula Id into its diastereomeric or enantiomeric forms and, optionally converting the compound of formula Id into a salt with a pharmaceutically acceptable acid.

27. The compound according to claim 1, wherein the functional group which can be converted to hydrogen in vivo is selected from acyl, carbamoyl, monoalkylated carbamoyl, dialkylated carbamoyl, dialkylated sulfonyl or alkoxycarbamoyl.

28. The compound according to claim 1, wherein the functional group which can be converted to hydrogen in vivo is selected from $C_{1-6}$-alkanoyl, aroly, $C_{1-6}$-alkylcarbamoyl, di-$C_{1-6}$-alkylcarbamoyl, $C_{1-6}$-alkoxycarbonyl, di-$C_{1-6}$-alkylsulfony or $C_{1-6}$-alkoxy-$C_{1-6}$-alkyl.

29. A compound of formula I

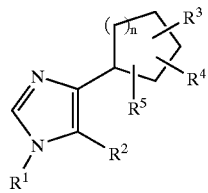

(I)

wherein the carbocyclic ring does or does not contain one or two double bonds;
n represents 1 or 2;
$R^1$ is hydrogen or a group which can be converted to hydrogen in vivo selected from acyl, carbamoyl, monoalkylated carbomoyl, dialkylated carbamoyl, dialkylated sulfonyl or alkoxycarbonyl;

$R^2$ is hydrogen, $C_{1-6}$-alkyl, cyano or halogen;
$R^3$ is hydrogen, hydroxy or halogen;
$R^4$ is hydrogen, hydroxy or cyano;
$R^5$ is
hydrogen;
aryl unsubstituted or substituted with halogen, $C_{1-6}$-alkoxy, $C_{1-6}$-alkyl, trifluoromethyl, $C_{3-8}$-cycloalkyl, aryl or heteroaryl;
$C_{1-6}$-alkyl unsubstituted or substituted with
$C_{3-8}$-cycloalkyl unsubstituted or substituted with halogen, $C_{1-6}$-alkoxy, $C_{1-6}$-alkyl, trifluoromethyl, $C_{3-8}$-cycloalkyl, aryl or heteroaryl;
aryl unsubstituted or substituted with halogen, $C_{1-6}$-alkoxy, $C_{1-6}$-alkyl, trifluoromethyl, $C_{3-8}$-cycloalkyl, aryl or heteroaryl; or
heteroaryl unsubstituted or substituted with halogen, $C_{1-6}$-alkoxy, $C_{1-6}$-alkyl, trifluoromethyl, $C_{3-8}$-cycloalkyl, aryl or heteroaryl;
—X—$R^6$ wherein X is —O— or —S—; and
$R^6$ is
hydrogen;
$C_{1-6}$-alkyl unsubstituted or substituted with halogen, $C_{1-6}$-alkoxy, trifluoromethyl, $C_{3-8}$-cycloalkyl, aryl or heteroaryl where the $C_{3-8}$-cycloalkyl, aryl and heteroaryl groups are unsubstituted or substituted with halogen, $C_{1-6}$-alkoxy, $C_{1-6}$-alkyl, trifluoromethyl, cyano, $C_{3-8}$-cycloalkyl, aryl or heteroaryl;
$C_{3-8}$-cycloalkyl unsubstituted or substituted with halogen, $C_{1-6}$alkoxy, $C_{1-6}$-alkyl, trifluoromethyl, $C_{3-8}$-cycloalkyl, aryl or heteroaryl;
aryl unsubstituted or substituted with halogen, $C_{1-6}$-alkoxy, $C_{1-6}$-alkyl, trifluoromethyl, cyano, $C_{3-8}$-cycloalkyl, aryl or heteroaryl;
heteroaryl unsubstituted or substituted with halogen, $C_{1-6}$-alkoxy, $C_{1-6}$-alkyl, trifluoromethyl, $C_{3-8}$-cycloalkyl, aryl or heteroaryl;
—$CONR^7R^8$ wherein $R^7$ and $R^8$ independently are
hydrogen;
$C_{1-6}$-alkyl unsubstituted or substituted with halogen, $C_{1-6}$-alkoxy, trifluoromethyl, $C_{3-8}$-cycloalkyl, aryl or heteroaryl where the $C_{3-8}$-cycloalkyl, aryl and heteroaryl groups are unsubstituted or substituted with halogen, $C_{1-6}$-alkoxy, $C_{1-6}$-alkyl, trifluoromethyl, cyano, $C_{3-8}$-cycloalkyl, aryl or heteroaryl;
$C_{3-8}$-cycloalkyl unsubstituted or substituted with halogen, $C_{1-6}$-alkoxy, $C_{1-6}$-alkyl, trifluoromethyl, $C_{3-8}$-cycloalkyl, aryl or heteroaryl;
aryl unsubstituted or substituted with halogen, $C_{1-6}$-alkoxy, $C_{1-6}$-alkyl, trifluoromethyl, cyano, $C_{3-8}$-cycloalkyl, aryl or heteroaryl; or
heteroaryl unsubstituted or substituted with halogen, $C_{1-6}$-alkoxy, $C_{1-6}$-alkyl, trifluoromethyl, $C_{3-8}$-cycloalkyl, aryl or heteroaryl; or
$R^7$ and $R^8$ together form a 3 to 8 membered, saturated or unsaturated carbocyclic or heterocyclic ring which is unsubstituted or substituted with halogen, $C_{1-6}$-alkoxy, $C_{1-6}$-alkyl, trifluoromethyl, $C_{3-8}$-cycloalkyl, aryl or heteroaryl; or
—$SO_2R^7$;
provided that when X is —S—, $R^6$ must not be hydrogen, —$CONR^7R^8$ or —$SO_2R^7$; or
—$CONR^7R^8$; or $R^4$ and $R^5$ taken together represent =O;
provided that
when $R^2$ is hydrogen, then $R^3$, $R^4$ or $R^5$ must not be methyl or ethyl in the 1 position;
when n is 2, $R^1$ is —CPh$_3$, $R^2$ and $R^3$ are hydrogen and $R^4$ is cyano in the 1 position, then $R^5$ must not be hydrogen;
when n is 2 and $R^1$, $R^2$, $R^3$ and $R^4$ are hydrogen, then $R^5$ must not be hydrogen; and
when n is 1 or 2, and $R^1$, $R^2$, $R^3$ and $R^4$ are hydrogen, then $R^5$ must not be hydroxy;
or any optical or geometric isomer or tautomeric form thereof or a pharmaceutically acceptable salt thereof.

30. A compound of formula I

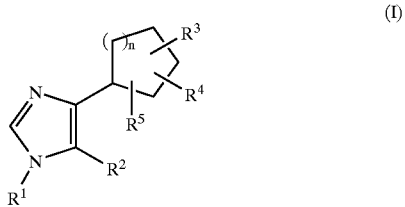

wherein the carbocyclic ring does or does not contain one or two double bonds;
n represents 1 or 2;
$R^1$ is hydrogen or a group which can be converted to hydrogen in vivo selected from $C_{1-6}$-alkanoyl, aroyl, $C_{1-6}$-alkyl-carbamoyl, di-$C_{1-6}$-alkylcarbamoyl, $C_{1-6}$-alkoxycarbonyl, di-$C_{1-6}$-alkylsulfonyl or $C_{1-6}$-alkoxy-$C_{1-6}$alkyl;
$R^2$ is hydrogen, $C_{1-6}$-alkyl, cyano or halogen;
$R^3$ is hydrogen, hydroxy or halogen;
$R^4$ is hydrogen, hydroxy or cyano;
$R^5$ is
hydrogen;
aryl unsubstituted or substituted with halogen, $C_{1-6}$-alkoxy, $C_{1-6}$-alkyl, trifluoromethyl, $C_{3-8}$-cycloalkyl, aryl or heteroaryl;
$C_{1-6}$-alkyl unsubstituted or substituted with
$C_{3-8}$-cycloalkyl unsubstituted or substituted with halogen, $C_{1-6}$-alkoxy, $C_{1-6}$-alkyl, trifluoromethyl, $C_{3-8}$-cycloalkyl, aryl or heteroaryl;
aryl unsubstituted or substituted with halogen, $C_{1-6}$-alkoxy, $C_{1-6}$-alkyl, trifluoromethyl, $C_{3-8}$-cycloalkyl, aryl or heteroaryl; or
heteroaryl unsubstituted or substituted with halogen, $C_{1-6}$-alkoxy, $C_{1-6}$-alkyl, trifluoromethyl, $C_{3-8}$-cycloalkyl, aryl or heteroaryl;
—X—$R^6$ wherein X is —O— or —S—; and
$R^6$ is
hydrogen;
$C_{1-6}$alkyl unsubstituted or substituted with halogen, $C_{1-6}$-alkoxy, trifluoromethyl, $C_{3-8}$-cycloalkyl, aryl or heteroaryl where the $C_{3-8}$-cycloalkyl, aryl and heteroaryl groups which are unsubstituted or substituted with halogen, $C_{1-6}$-alkoxy, $C_{1-6}$-alkyl, trifluoromethyl, cyano, $C_{3-8}$-cycloalkyl, aryl or heteroaryl;
$C_{3-8}$-cycloalkyl unsubstituted or substituted with halogen, $C_{1-6}$-alkoxy, $C_{1-6}$-alkyl, trifluoromethyl, $C_{3-8}$-cycloalkyl, aryl or heteroaryl;
aryl unsubstituted or substituted with halogen, $C_{1-6}$-alkoxy, $C_{1-6}$-alkyl, trifluoromethyl, cyano, $C_{3-8}$-cycloalkyl, aryl or heteroaryl;
heteroaryl unsubstituted or substituted with halogen, $C_{1-6}$-alkoxy, $C_{1-6}$-alkyl, trifluoromethyl, $C_{3-8}$-cycloalkyl, aryl or heteroaryl;
—CONR$^7$R$^8$ wherein $R^7$ and $R^8$ independently are
hydrogen;
$C_{1-6}$-alkyl unsubstituted or substituted with halogen, $C_{1-6}$-alkoxy, trifluoromethyl, $C_{3-8}$-cycloalkyl, aryl or heteroaryl where the $C_{3-8}$-cycloalkyl, aryl and heteroaryl groups are unsubstituted or substituted with halogen, $C_{1-6}$-alkoxy, $C_{1-6}$-alkyl, trifluoromethyl, cyano, $C_{3-8}$-cycloalkyl, aryl or heteroaryl;
$C_{3-8}$-cycloalkyl unsubstituted or substituted with halogen, $C_{1-6}$-alkoxy, $C_{1-6}$-alkyl, trifluoromethyl, $C_{3-8}$-cycloalkyl, aryl or heteroaryl;
aryl unsubstituted or substituted with halogen, $C_{1-6}$-alkoxy, $C_{1-6}$-alkyl, trifluoromethyl, cyano, $C_{3-8}$-cycloalkyl, aryl or heteroaryl; or
heteroaryl unsubstituted or substituted with halogen, $C_{1-6}$-alkoxy, $C_{1-6}$-alkyl, trifluoromethyl, $C_{3-8}$-cycloalkyl, aryl or heteroaryl; or
$R^7$ and $R^8$ together form a 3 to 8 membered, saturated or unsaturated carbocyclic or heterocyclic ring which is unsubstituted or substituted with halogen, $C_{1-6}$-alkoxy, $C_{1-6}$-alkyl, trifluoromethyl, $C_{3-8}$-cycloalkyl, aryl or heteroaryl; or
—SO$_2$R$^7$;
provided that when X is —S—, $R^6$ must not be hydrogen, —CONR$^7$R$^8$ or —SO$_2$R$^7$; or
—CONR$^7$R$^8$; or
$R^4$ and $R^5$ taken together represent =O;
provided that
when $R^2$ is hydrogen, then $R^3$, $R^4$ or $R^5$ must not be methyl or ethyl in the 1 position;
when n is 2, $R^1$ is —CPh$_3$, $R^2$ and $R^3$ are hydrogen and $R^4$ is cyano in the 1 position, then $R^5$ must not be hydrogen;
when n is 2 and $R^1$, $R^2$, $R^3$ and $R^4$ are hydrogen, then $R^5$ must not be hydrogen; and
when n is 1 or 2, and $R^1$, $R^2$, $R^3$ and $R^4$ are hydrogen, then $R^5$ must not be hydroxy;
or any optical or geometric isomer or tautomeric form thereof or a pharmaceutically acceptable salt thereof.

* * * * *